(12) United States Patent
Imai et al.

(10) Patent No.: US 9,919,107 B2
(45) Date of Patent: Mar. 20, 2018

(54) LIQUID ADMINISTRATION DEVICE

(71) Applicant: Terumo Kabushiki Kaisha, Tokyo (JP)

(72) Inventors: Masaomi Imai, Chuo (JP); Shigeaki Fuke, Fujinomiya (JP); Manabu Arinobe, Hadano (JP); Kenji Handa, Hiratsuka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 311 days.

(21) Appl. No.: 14/661,728

(22) Filed: Mar. 18, 2015

(65) Prior Publication Data

US 2015/0190580 A1 Jul. 9, 2015

Related U.S. Application Data

(63) Continuation of application No. PCT/JP2014/050246, filed on Jan. 9, 2014.

(30) Foreign Application Priority Data

| Jan. 15, 2013 | (JP) | ................................. 2013-004992 |
| May 10, 2013 | (JP) | ................................. 2013-100716 |

(51) Int. Cl.
*A61M 5/28* (2006.01)
*A61M 5/315* (2006.01)
(Continued)

(52) U.S. Cl.
CPC .... *A61M 5/31505* (2013.01); *A61M 5/31513* (2013.01); *A61M 5/3202* (2013.01);
(Continued)

(58) Field of Classification Search
CPC ............ A61M 2005/208; A61M 5/326; A61M 2005/206; A61M 5/24; A61M 5/3202;
(Continued)

(56) References Cited

U.S. PATENT DOCUMENTS 5,084,017 A * 1/1992 Maffetone ........... A61M 5/5066
604/110
5,242,400 A * 9/1993 Blake, III ............. A61M 5/322
604/110
(Continued)

FOREIGN PATENT DOCUMENTS

| CN | 101312759 | 4/2013 |
| JP | 2008-525059 A | 7/2008 |

(Continued)

OTHER PUBLICATIONS

International Search Report dated Apr. 15, 2014 issued in PCT/JP2014/050246.

(Continued)

*Primary Examiner* — Gerald Landry, II
(74) *Attorney, Agent, or Firm* — Foley & Lardner LLP

(57) ABSTRACT

A liquid administration device includes an inner structure that includes a cylindrical body that has a bottom part in a distal portion thereof and an opening portion in a proximal portion thereof, a needle tube that is mounted in the distal portion of the cylindrical body and has a sharp needle tip at a distal end and a proximal end of which is communicatable with an inside of the cylindrical body, and a gasket that is located in the cylindrical body; an operation member that includes a plunger, the operation member being configured to perform a pressing operation in which the plunger is moved relative to the cylindrical body in a distal direction while being pressed; an engagement portion that includes: a first engagement portion and a second engagement portion.

17 Claims, 29 Drawing Sheets

(51) Int. Cl.
*A61M 5/32* (2006.01)
*A61M 5/20* (2006.01)
*A61M 5/31* (2006.01)

(52) U.S. Cl.
CPC ........... *A61M 5/326* (2013.01); *A61M 5/3272* (2013.01); *A61M 2005/206* (2013.01); *A61M 2005/2013* (2013.01); *A61M 2005/2026* (2013.01); *A61M 2005/3103* (2013.01); *A61M 2005/3267* (2013.01)

(58) Field of Classification Search
CPC ................ A61M 5/322; A61M 5/3234; A61M 2005/202; A61M 2005/2407; A61M 2005/2496; A61M 2005/3267
USPC ....... 604/110, 131, 187, 192, 195, 210, 218, 604/228, 240
See application file for complete search history.

(56) References Cited

U.S. PATENT DOCUMENTS

| | | | | |
|---|---|---|---|---|
| 9,227,018 | B2* | 1/2016 | Ogawa | A61M 5/28 |
| 2001/0005781 | A1* | 6/2001 | Bergens | A61M 5/2033 |
| | | | | 604/208 |
| 2003/0004467 | A1* | 1/2003 | Musick | A61M 5/284 |
| | | | | 604/218 |
| 2008/0255513 | A1* | 10/2008 | Kaal | A61M 5/3234 |
| | | | | 604/110 |
| 2008/0262423 | A1* | 10/2008 | Ingram | A61M 5/31501 |
| | | | | 604/110 |
| 2009/0124995 | A1* | 5/2009 | Bruce | A61M 5/1458 |
| | | | | 604/506 |
| 2010/0010472 | A1* | 1/2010 | Moore | A61M 5/31596 |
| | | | | 604/520 |
| 2011/0092915 | A1 | 4/2011 | Olson et al. | |
| 2012/0197232 | A1 | 8/2012 | Lee et al. | |
| 2013/0138049 | A1* | 5/2013 | Kemp | A61M 5/2033 |
| | | | | 604/197 |
| 2013/0150800 | A1* | 6/2013 | Kemp | A61M 5/2033 |
| | | | | 604/192 |
| 2013/0274671 | A1* | 10/2013 | Jennings | A61M 5/20 |
| | | | | 604/154 |
| 2014/0364812 | A1* | 12/2014 | Lumme | A61M 5/2033 |
| | | | | 604/198 |
| 2015/0088079 | A1* | 3/2015 | Butler | A61M 5/31543 |
| | | | | 604/211 |
| 2015/0133872 | A1* | 5/2015 | Smith | A61M 5/20 |
| | | | | 604/218 |

FOREIGN PATENT DOCUMENTS

| | | |
|---|---|---|
| JP | 4287611 B2 | 7/2009 |
| WO | WO-2006/066336 | 6/2006 |
| WO | WO-2012/000835 | 1/2012 |
| WO | WO-2012/003516 | 1/2012 |
| WO | WO-2012/117837 | 9/2012 |
| WO | WO-2012/158096 | 11/2012 |

OTHER PUBLICATIONS

European Search Reported issued in European Patent Application No. 14740539.3 dated Sep. 1, 2016.

* cited by examiner

LIQUID ADMINISTRATION DEVICE

CROSS-REFERENCE TO RELATED APPLICATIONS

This application is a continuation application filed under 35 U.S.C. 111(a) claiming the benefit under 35 U.S.C. § § 120 and 365(c) of PCT International Application No. PCT/JP2014/050246 filed on Jan. 9, 2014, which is based upon and claims the benefit of priority of Japanese Application No. 2013-004992 filed on Jan. 15, 2013 and Japanese Application No. 2013-100716 filed on May 10, 2013, the entire contents of which are hereby incorporated by reference in their entireties.

BACKGROUND

Technical Field

The present disclosure relates to a liquid administration device.

Background Art

Conventionally, a prefilled syringe that is sterilely filled with a drug solution and can administer the drug solution has been known.

The prefilled syringe comprises a syringe outer cylinder which has an opening part through which the drug solution is discharged; a needle tube that is provided in the opening part of the syringe outer cylinder and has a sharp needle tip at a distal end of the needle tube; a gasket that is slidable in the syringe outer cylinder; a drug solution with which a space surrounded by the syringe outer cylinder and the gasket is filled; and a plunger which is interlocked with the gasket on a proximal side and discharges the drug solution through the opening part by pressing the gasket toward the distal direction. When administering the drug solution using the prefilled syringe, a living body is punctured with the needle tube, and the pressing operation of the plunger is performed in the punctured state. As a result, the drug solution is discharged from the opening part by the gasket. Accordingly, the drug solution can be administered to the living body through the needle tube.

However, the pressing operation of the plunger of the prefilled syringe can be performed at an arbitrary timing depending on a user. Therefore, there has been a concern that the pressing operation of the plunger may be erroneously performed before the living body is punctured with the needle tube. In this case, the drug solution unintentionally leaks from the needle tube, or in some cases, it is difficult to administer a sufficient amount of the drug solution to the living body since the drug solution is insufficient due to the leakage.

In order to prevent the above-described unintentional leakage of the drug solution from the needle tube, Japanese Patent No. 4287611 discloses a liquid administration device including a mechanism for inhibiting the pressing operation of the plunger using a coupling element. According to such a liquid administration device, when the pressing operation of the plunger is performed with force stronger than a predetermined threshold value, the coupling element moves in the distal direction and comes into contact with a predetermined part in the syringe outer cylinder. Accordingly, the state where the movement of the plunger is inhibited by the coupling element is released, and the plunger enters a state where the pressing operation of the plunger can be performed.

However, the liquid administration device disclosed in Japanese Patent No. 4287611 is configured such that the state where the movement of the plunger is inhibited by the coupling element is released by the coupling element moving in the axial direction. Therefore, there is a concern that the state where the movement of the plunger is inhibited by the coupling element cannot be maintained because the coupling element can move in the distal direction through the pressing operation of the plunger, even though it is unnecessary to move the plunger yet.

SUMMARY OF INVENTION

One objective of certain embodiments of the present invention is to provide a liquid administration device with which it is possible to reliably prevent erroneous operation of an operation member.

According to one embodiment, a liquid administration device includes: an inner structure that includes a cylindrical body which has a bottom part in a distal portion and an opening portion in a proximal portion and can be filled with a liquid therein, a needle tube which is mounted in the distal portion of the cylindrical body and has a sharp needle tip at a distal end and a proximal end of which is communicatable with the inside of the cylindrical body, and a gasket which is installed in the cylindrical body and is slidable along an axial direction of the cylindrical body; an operation member that has a plunger configured to press the gasket and perform a pressing operation in which the plunger is moved relative to the cylindrical body toward a distal direction while being pressed; an engagement portion that includes a first engagement portion that is provided in one of the inner structure and the operation member and a second engagement portion that is provided in the other one of the inner structure and the operation member, the engagement portion configured to enter an engagement state where the pressing operation is inhibited when the first engagement portion and the second engagement portion are engaged with each other and enter a released state where the pressing operation can be performed when the engagement state is released; and a rotary portion which makes the first engagement portion and the second engagement portion, being in the engagement state, relatively rotate around a central axis of the inner structure and enter the released state.

In one aspect, the liquid administration device further includes: a rotation inhibiting portion that inhibits the relative rotation of the first engagement portion and the second engagement portion around the central axis of the inner structure in the engagement state.

In one aspect, the plunger has a plate-shaped part which forms an elongated shape, and the first engagement portion has at least one stepped portion in which the width of the plate-shaped part is changed.

In one aspect, the second engagement portion has at least one protruding portion which protrudes toward the inside of the cylindrical body.

In one aspect, the second engagement portion has a slope, which is provided at a distal portion of the protruding portion and on which the first engagement portion abuts, as the rotary portion.

In one aspect, the cylindrical body has an inner cylinder that has an opening portion in the proximal portion and can be filled with a liquid therein and an outer cylinder that is concentrically disposed with the inner cylinder on an outer peripheral side of the inner cylinder and is installed so as to be relatively rotatable with respect to the inner cylinder around the central axis.

In one aspect, the rotary portion has a slope that is provided on the second engagement portion and on which the first engagement portion abuts, and the outer cylinder is constituted so as to relatively rotate with respect to the operation member around the central axis of the outer cylinder due to the first engagement portion relatively moving to the second engagement portion along the slope.

In one aspect, the liquid administration device further includes a cover member which is movable between a position (A) at which at least the needle tip of the needle tube is covered and a position (B) at which the needle tip is exposed by the cover member being retreated from the position (A) in a proximal direction and at which a liquid is discharged through the needle tube.

In one aspect, the engagement portion is constituted so as to enter an engagement state when the cover member is positioned at the position (A) and enter a released state when the engagement state is released by the cover member moving to the position (B).

In one aspect, the rotary portion has a spur which is provided in any one of the cover member and the outer cylinder, and an inclined first groove which is provided in the other one of the cover member and the outer cylinder and into which the spur is inserted, and the outer cylinder is constituted so as to be relatively rotated with respect to the cover member around the central axis by the spur relatively moving to the cover member along the first groove, and as a result, the outer cylinder is relatively rotated with respect to the operation member around the central axis of the outer cylinder.

In one aspect, the rotary portion has a third biasing member that biases any one of the first engagement portion and the second engagement portion to the other one of the first engagement portion and the second engagement portion in a rotational direction of the inner structure around the central axis.

In one aspect, the third biasing member is twisted in an initial state.

In certain embodiments of the liquid administration device, it is preferable that the rotation inhibiting portion is provided to enable the relative movement of the cover member to the inner structure in the axial direction of the inner structure in the engagement state and to inhibit the relative rotation of the first engagement portion and the second engagement portion around the central axis of the inner structure; the rotation inhibiting portion has a second groove which communicates with one end portion of the first groove and extends in the axial direction of the outer cylinder; and when the cover member is positioned in the position (A), the spur is inserted into the second groove. Accordingly, the outer cylinder is inhibited from being relatively rotated with respect to the cover member around the central axis, and as a result, the outer cylinder is inhibited from being relatively rotated with respect to the operation member.

In certain embodiments, the liquid administration device is constituted such that the cover member moves relative to the operation member in the proximal direction and the outer cylinder moves relative to the cover member in the axial direction when the operation member is pressed in the distal direction while the distal portion of the cover member abuts on a living body, and at this time, the spur moves relative to the cover member along the second groove.

In certain embodiments, it is preferable that the liquid administration device is constituted such that the groove has a third groove that communicates with the other end portion of the first groove and extends in the axial direction of the outer cylinder, and as a result, the cover member can move relative to the outer cylinder in the axial direction after discharge of the liquid is completed.

In certain embodiments of the liquid administration device, it is preferable that the slope is directed in a tangential direction of a circle which has the central axis of the inner structure as a center and passes through the slope when seen in a plan view.

According to certain embodiments of the present invention, the first engagement portion and the second engagement portion that are in the engagement state are configured to relatively rotate around the central axis of the inner structure to be set to the released state. Therefore, the direction of relative displacement of the first engagement portion and the second engagement portion, when making them enter the released state, is different from the direction of the pressing operation of the operation member. Accordingly, it is possible to prevent the first engagement portion and the second engagement portion from unintentionally entering the released state and to prevent a liquid from unintentionally leaking from the needle tube before or in the middle of puncturing of the skin with the needle tube.

DETAILED DESCRIPTION

Hereinafter, embodiments of a liquid administration device according to the present invention will be described in detail based on the embodiment shown in the attached drawings.

First Embodiment

Figure 1:
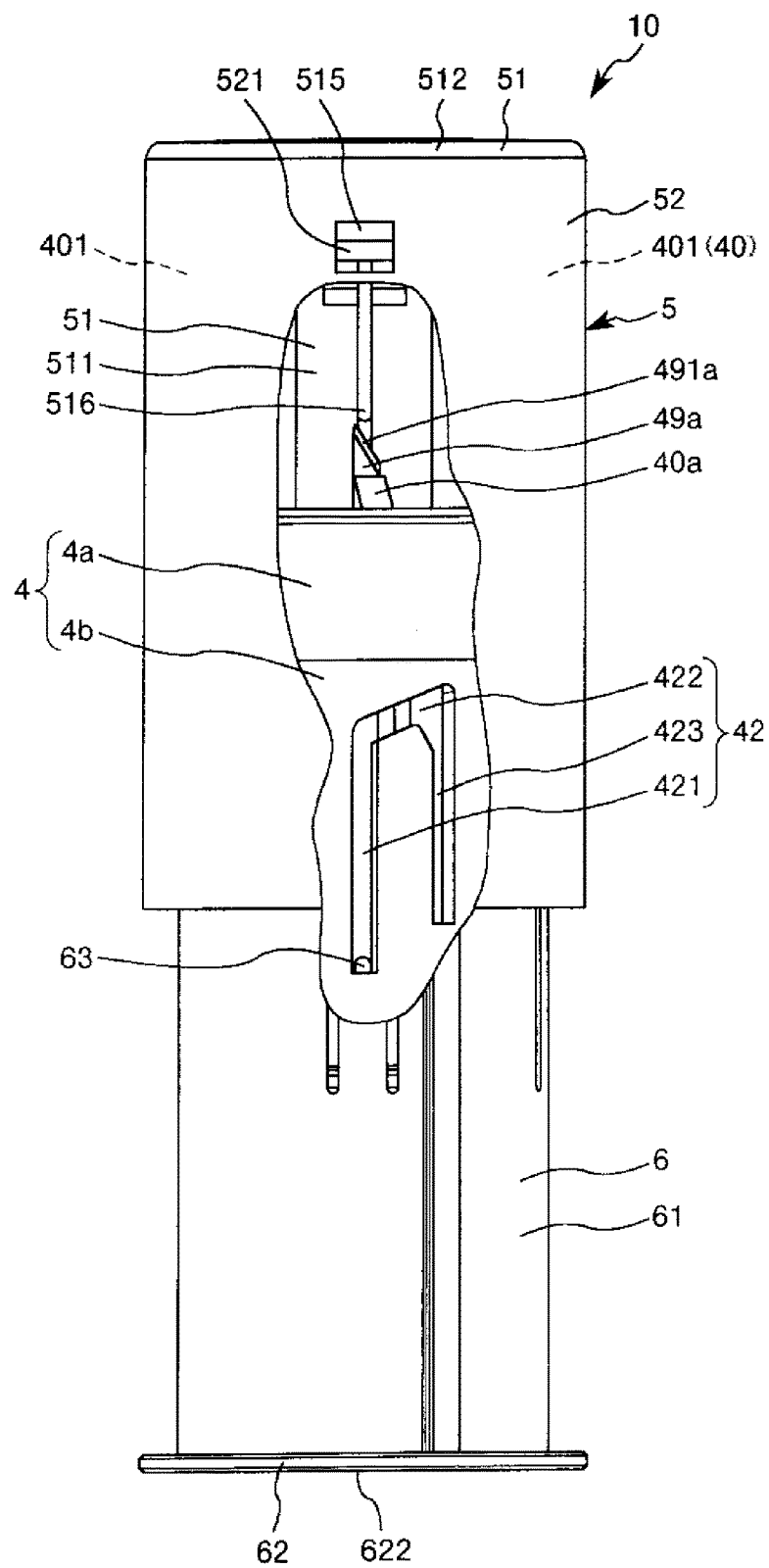
FIG. 1 is a side view showing a first embodiment of a liquid administration device of the present invention.
Figure 2:
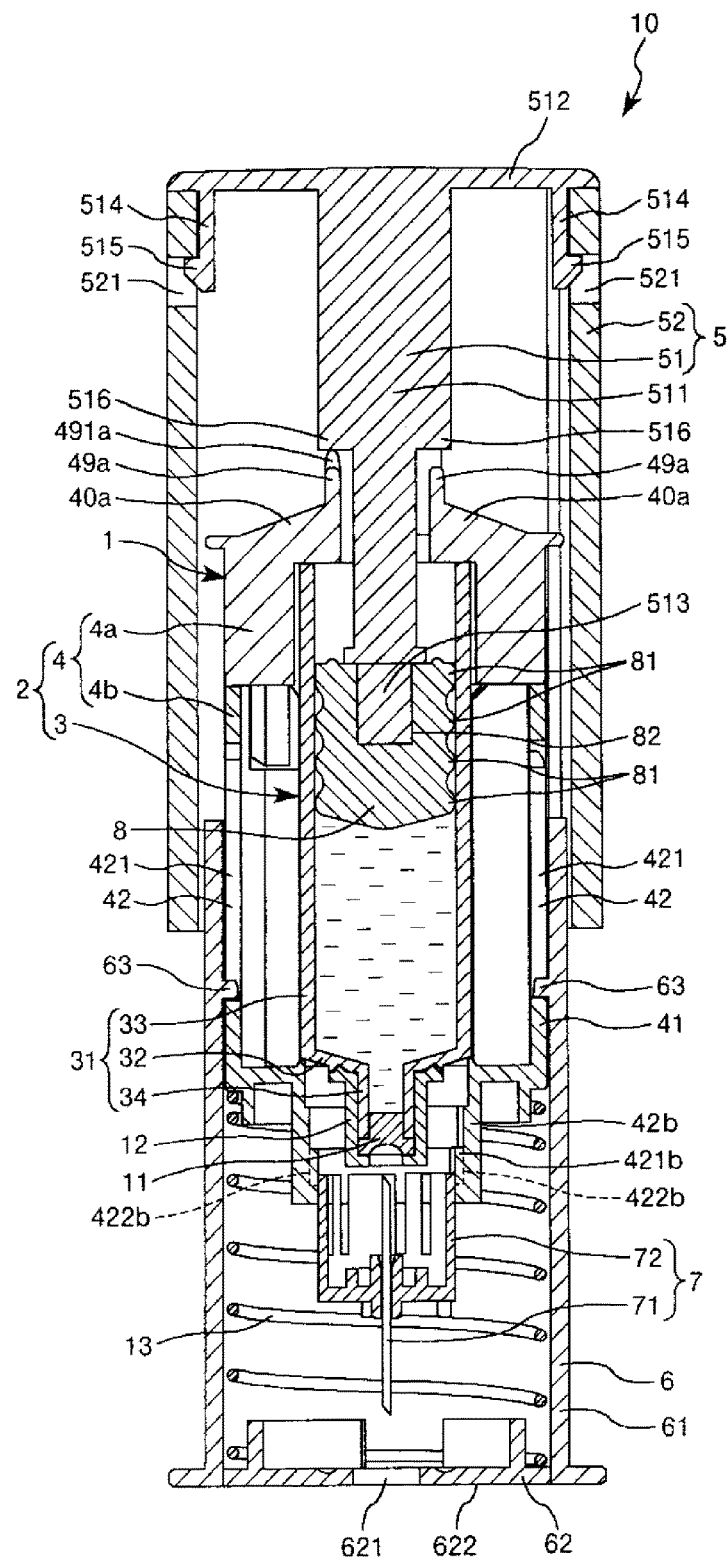
FIG. 2 is a longitudinal sectional view of the liquid administration device shown in FIG. 1.
Figure 3:
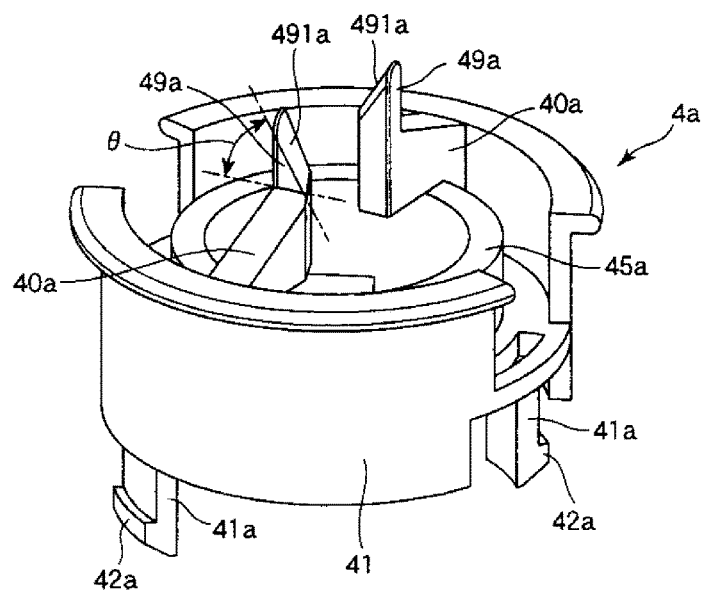
FIG. 3 is a perspective view of a proximal side member of an outer cylinder of a cylindrical body of the liquid administration device shown in FIG. 1.
Figure 4:
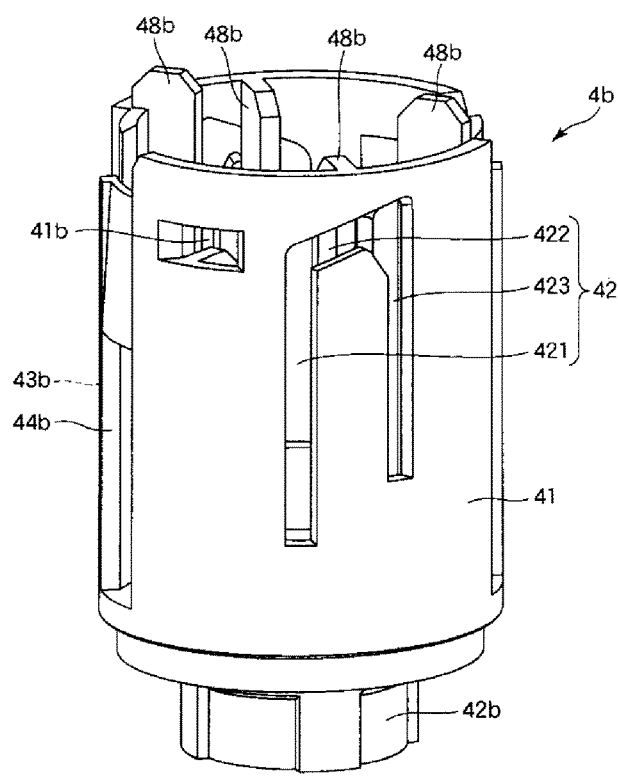
FIG. 4 is a perspective view of a distal side member of the outer cylinder of the cylindrical body of the liquid administration device shown in FIG. 1.
Figure 5:
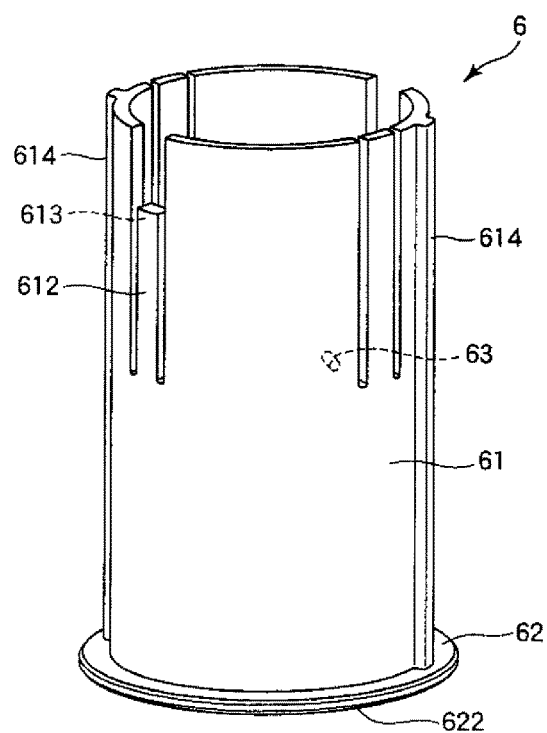
FIG. 5 is a perspective view of a cover member of the liquid administration device shown in FIG. 1.
Figure 6:
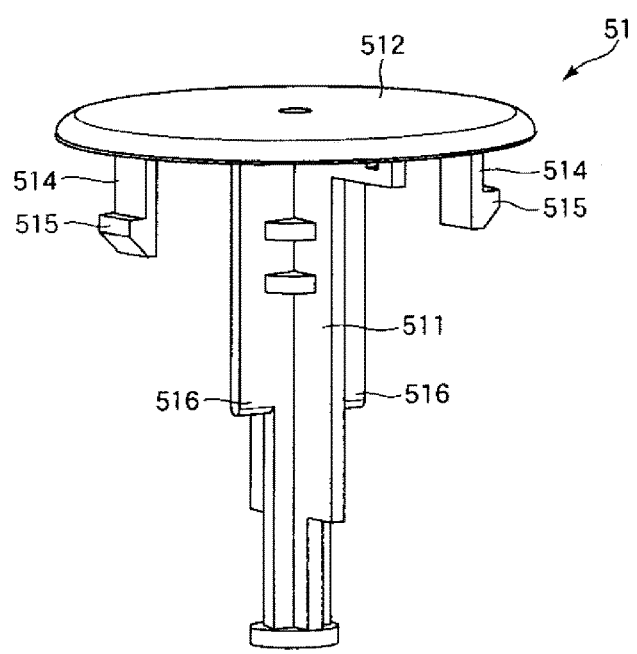
FIG. 6 is a perspective view of a plunger of the liquid administration device shown in FIG. 1.

FIG. 1 is a side view showing a first embodiment of a liquid administration device of the present invention. FIG. 2 is a longitudinal sectional view of the liquid administration device shown in FIG. 1. FIG. 3 is a perspective view of a proximal side member of an outer cylinder of a cylindrical body of the liquid administration device shown in FIG. 1. FIG. 4 is a perspective view of a distal side member of the outer cylinder of the cylindrical body of the liquid administration device shown in FIG. 1. FIG. 5 is a perspective view of a plunger of the liquid administration device shown in FIG. 1. FIG. 6 is a perspective view of a cover member of the liquid administration device shown in FIG. 1. Each of FIGS. 7, 9, 11, and 13 is a side view showing an operation state in use of the liquid administration device shown in FIG. 1 in order. Each of FIGS. 8, 10, 12, 14, and 15 is a longitudinal sectional view showing the operation state in use of the liquid administration device shown in FIG. 1 in order. Note that, hereinafter, the upper side is described as "proximal end (rear end)" or "upper (upward)", the lower side is described as "distal end" or "lower (downward), and the vertical direction is described as "axial direction" or "longitudinal direction" in FIGS. 1 to 15.

The liquid administration device 10 shown in FIGS. 1, 2, and 7 to 15 is a medical device used when administering (injecting) a liquid into a living body. Note that the liquid is appropriately selected according to its purpose of use, and examples thereof include drug solutions, mainly injected hypodermically, such as hematopoietic agents, vaccines, hormone preparations, antirheumatic agents, anticancer agents, anesthetics, and anticoagulants.

The liquid administration device 10 includes an inner structure (structure) 1; an operation member 5; a cover member 6 that is disposed on an outer peripheral side of the inner structure 1; a coil spring 13 that is a first biasing member for biasing the cover member 6 in the distal direction; and an auxiliary mechanism (auxiliary portion) 40.

As shown in FIG. 2, the inner structure 1 includes a cylindrical body 2 that is configured to have an inner cylinder 3 and an outer cylinder 4; a puncture needle 7 that is configured to have a double ended needle (needle tube) 71 and a support member 72; and a gasket 8 that is installed in the inner cylinder 3 (cylindrical body 2) and is slidable along the axial direction of the inner cylinder 3.

As shown in FIG. 2, the inner cylinder 3 has an inner cylinder body 31. The inner cylinder body 31 is configured to have a bottom part 32 in the distal portion; a side wall 33 that is erected from the edge of the bottom part 32; and a member that has an opening portion in a proximal portion, that is, a member forming a bottomed cylindrical shape. The inside of the inner cylinder 3 can be filled with a liquid. In addition, an opening part 34, of which the diameter is decreased with respect to a part of the side wall 33 of the inner cylinder body 31 and through which a liquid passes, is integrally formed in a protruding manner on the distal portion of the inner cylinder body 31, that is, in a central portion of the bottom part 32. A liquid is sucked in or discharged from the opening part 34.

In addition, the inner cylinder 3 has a sealing member (sealing portion) 11 that liquid-tightly seals the opening part 34 of the inner cylinder body 31 and a fixing member 12 that fixes the sealing member 11 from its distal side.

The sealing member 11 is formed of an elastic body, and a convex portion is formed on its proximal surface. The opening part 34 is liquid-tightly sealed by liquid-tightly fitting the convex portion to the opening part 34.

The fixing member 12 is a cylindrical member. The fixing member 12 fits to the sealing member 11 and the opening part 34 from their outer peripheral side and fixes the sealing member 11 to the inner cylinder body 31. Accordingly, removal of the sealing member 11 from the inner cylinder body 31 is reliably prevented. Note that a method by bonding or welding may also be used as the method of fixing the fixing member 12.

In addition, constituent materials for the inner cylinder body 31, the fixing member 12, the outer cylinder 4, the cover member 6, the support member 72, and the operation member 5 are not particularly limited, and examples thereof include various types of resins such as polyvinyl chloride, polyethylene, polypropylene, cyclic polyolefin, polystyrene, poly-(4-methylpentene-1), polycarbonate, acrylic resins, acrylonitrile-butadiene-styrene copolymers, polyesters such as polyethylene terephthalate and polyethylene naphthalate, butadiene-styrene copolymers, and polyamides (for example, nylon 6, nylon 6-6, nylon 6-10 and nylon 12). Among these, resins such as polypropylene, cyclic polyolefin, polyesters and poly-(4-methylpentene-1) are preferable in view of the ease in molding.

In addition, elastic materials constituting the sealing member 11 and the gasket 8 are not particularly limited, and examples thereof include elastic materials such as various rubber materials such as natural rubber, butyl rubber, isoprene rubber, butadiene rubber, styrene-butadiene rubber, and silicone rubber; various types of thermoplastic elastomers, such as polyurethane, polyester, polyamide, olefin, and styrene elastomers; or mixtures thereof.

The outer cylinder 4 is concentrically disposed with the inner cylinder 3 on the outer peripheral side of the inner cylinder 3. As shown in FIGS. 2 to 4, the whole shape of the outer cylinder 4 forms a cylindrical shape in which both ends are opened, and the length of the outer cylinder is longer than the inner cylinder 3. In addition, the outer cylinder 4 is made to be rotationally movable with respect to the inner cylinder 3 by having its axis as a center.

The outer cylinder 4 is configured to have a proximal side member 4a that is disposed on the proximal side and shown in FIG. 3; and a distal side member 4b that is disposed on the distal side and shown in FIG. 4. A pair of hole portions 41b that is disposed so as to face each other is formed on the proximal side of the distal side member 4b. In addition, a pair of elastic arm portions 41a that is disposed so as to face each other is protrusively formed on the distal side of the proximal side member 4a in the distal direction, and a claw 42a which protrudes outward is formed in the distal portion of each of the arm portions 41a. The claws 42a are inserted into the hole portions 41b from the inside of the proximal side of the distal side member 4b, and the claws 42a and the hole portions 41b are engaged, thereby interlocking the proximal side member 4a and the distal side member 4b.

Note that the methods of interlocking the proximal side member 4a and the distal side member 4b are not particularly limited, and examples thereof include fusion such as adhesive heat fusion using adhesives, solvents, or the like, high frequency fusion, and ultrasonic fusion.

In addition, the outer cylinder 4 has a body section 41; a decreased diameter portion 42b that is formed on the distal side of the body section 41 and in which the diameter is decreased with respect to the body section 41; and a decreased diameter portion 45a that is formed in the proximal portion of the body section 41 and in which the diameter is decreased with respect to the body section 41.

A stepped portion 421b is formed in an inner peripheral part of the decreased diameter portion 42b. In addition, four grooves 422b are formed in the inner peripheral part of the decreased diameter portion 42b (refer to FIG. 2). The grooves 422b are arranged at equiangular intervals in parallel along a circumferential direction of the decreased diameter portion 42b. Note that the decreased diameter portion 45a is formed in the present embodiment, but the decreased diameter portion 45a may not be formed.

In addition, a pair of long holes 43b and a pair of long holes 44b that penetrate the body section 41 are formed on the body section 41 of the distal side member 4b. The long holes 43b are disposed so as to face each other, and similarly, the long holes 44b are also disposed so as to face each other. Note that each of the long holes 43b has an identical shape, and therefore, one long hole 43b will be representatively described hereinafter. Similarly, each of the long holes 44b has an identical shape, and therefore, one long hole 44b will be representatively described hereinafter. Note that the long hole 43b penetrates the body section in the present embodiment, but may be sunken without penetrating the body section and the same effect can be obtained even in this case (not shown).

In addition, the long holes 43b and 44b are arranged in parallel along the circumferential direction of the body section 41. Note that, in the present embodiment, as shown in FIG. 4, the long hole 43b is disposed on the left side of the long hole 44b.

In addition, the long holes 43b and 44b extend along an axis of the body section 41. The end surface of the long hole 43b on the proximal side is positioned further on the distal side than the end surface of the long hole 44b on the proximal side. In addition, the end surface of the long hole 43b on the proximal side is made into a slope which is inclined at a predetermined angle with respect to the axis of the body section 41. In contrast, the end surface of the long hole 44b on the proximal side is set to be perpendicular to the axis of the body section 41.

In addition, a pair of protruding portions 40a is formed on the proximal side of the body section 41 of the proximal side member 4a. The protruding portions 40a are disposed so as to face each other. The protruding portions 40a are protrusively formed toward the inside, that is, toward a central axis from the inner peripheral surface of the body section 41.

In addition, a spur (second engagement portion) 49a is protrusively formed in an end portion (distal portion) of each of the protruding portions 40a on the central axis side toward the proximal direction.

Each of the spurs 49a has a slope 491a on which each of the stepped portions 516, to be described later, abut as a rotary mechanism (rotary portion). The rotary mechanism makes the stepped portion 516 and the spur 49a that are in an engagement state relatively rotate around the central axis of the inner structure 1 and enter a released state. The slope 491a is a plane in the configuration shown in the drawing. The slope 491a faces a tangential direction of a circle which has the central axis of the inner structure 1 as a center and passes through the slope 491a when seen in a plan view. Accordingly, the outer cylinder 4 relatively rotates with respect to the operation member 5 around the central axis of the outer cylinder 4 due to the stepped portion 516 moving relative to the spur 49a along the slope 491a.

In addition, the inclination angle θ of the slope 491a is not particularly limited and can be appropriately set depending on the conditions. The inclination angle θ thereof is preferably 5° to 85° and more preferably 20° to 70°.

Note that the shape of the slope 491a may be a curved surface without being limited to the plane.

In addition, the number of protruding portions 40a are not limited to two, and examples thereof may include one or three or greater.

Figure 10:
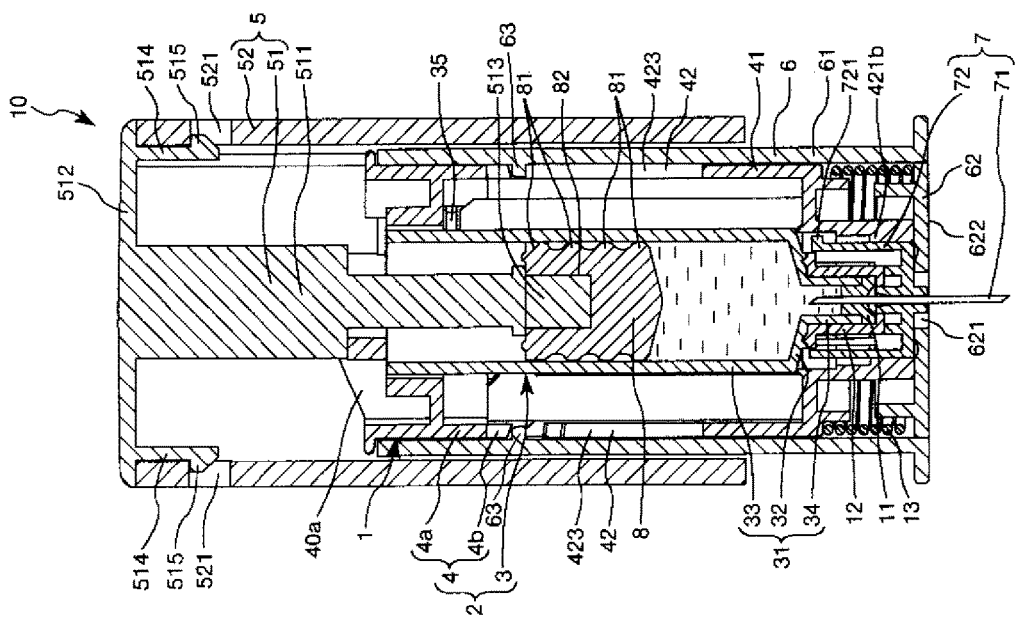
FIG. 10 is a longitudinal sectional view showing the operation state in use of the liquid administration device shown in FIG. 1 in order, when the cover member is in the third position.

Note that the inner cylinder 3 is installed between each of the protruding portions 40a and the decreased diameter portion 42b, of the outer cylinder 4, and movement of the inner cylinder 3 relative to the outer cylinder 4 in the axial direction is inhibited by a pair of flanges (protruding pieces) 35 of the inner cylinder 3 being interposed between an upper end surface inside the distal side of the proximal side member 4a of the outer cylinder 4 and the upper end surface of a longitudinal rib 48b inside the distal side member 4b of the outer cylinder 4 from upper and lower sides as shown in FIG. 10. Note that only one of the pair of flanges 35 of the inner cylinder 3 is shown in FIG. 10.

In addition, as shown in FIGS. 1 and 4, a pair of cam grooves 42, into which a pair of spurs 63 of the cover member 6 to be described later is inserted, is formed on the outer peripheral surface of the body section 41 of the outer cylinder 4. In the present embodiment, each of the cam grooves 42 is formed so as to penetrate through a wall part of the body section 41. However, each of the cam grooves is not limited thereto and may not penetrate the wall part of the body section 41. Note that the cam grooves 42 are the same as each other, and therefore, one cam groove 42 will be representatively described below.

The cam groove 42 is configured to have a linear groove (second groove) 421 which extends in the axial direction of the outer cylinder 4 and is linearly formed on the outer peripheral surface of the body section 41; an inclined groove (first groove) 422 which is formed on the outer peripheral surface of the body section so as to be inclined at a predetermined angle with respect to the axis of the outer cylinder 4; and a linear groove (third groove) 423 which extends in the axial direction of the outer cylinder 4 and is linearly formed on the outer peripheral surface of the body section 41. The distal portion of the linear groove 423 is positioned further on the proximal side than the distal portion of the linear groove 421, and the proximal portion of the linear groove 423 is positioned further on the proximal side than the proximal portion of the linear groove 421. In addition, the inclined groove 422 is formed to be shorter than one turn.

The linear groove 421, the inclined groove 422, and the linear groove 423 are continuously formed from the left side to the right side in FIG. 1. The proximal portion of the linear groove 421 communicates with the distal portion (end portion on the left side in FIG. 1) of the inclined groove 422, and the proximal portion (end portion on the right side in FIG. 1) of the inclined groove 422 communicates with the proximal portion of the linear groove 423.

When the cover member 6 moves in the axial direction of the outer cylinder 4, due to the cam groove 42 and the spur 63 of the cover member 6, the outer cylinder 4 is rotated at a predetermined angle with respect to the cover member 6 and the inner cylinder 3 to the right side in FIG. 1. That is, the outer cylinder 4 is relatively rotated with respect to the cover member 6 around the central axis due to the spur 63 relatively moving the cover member 6 along the inclined groove 422. As a result, the outer cylinder 4 is relatively rotated with respect to the operation member 5 around the central axis of the outer cylinder 4. Accordingly, the rotary mechanism (rotary portion) is constituted by the spur 63 and the inclined groove 422.

In addition, when the cover member 6 is at a position (A) to be described later, the spur 63 is disposed in the linear groove 421, and accordingly, the outer cylinder 4 is inhibited from being relatively rotated with respect to the cover member 6 around the central axis. As a result, the outer cylinder 4 is inhibited from being relatively rotated with respect to the operation member 5. Accordingly, a rotation inhibiting mechanism (rotation inhibiting portion) that inhibits relative rotation of the stepped portion (first engagement portion) 516 and the spur (second engagement portion) 49a around the central axis of the inner structure 1 in an engagement state is configured by the spur 63 and the linear groove 421.

Note that the grooves may be provided in the cover member 6 and the spur may be provided in the outer cylinder 4.

As shown in FIG. 2, a puncture needle 7 is disposed in the distal portion of the cylindrical body 2. The puncture needle 7 is configured to have a double ended needle 71 and a support member 72 which supports and fixes the double ended needle 71.

The double ended needle 71 is a hollow needle tube, has a sharp distal side needle tip at a distal end, and has a sharp proximal side needle tip at a proximal end. The double ended needle 71 can puncture a living body with the distal side needle tip and can puncture the sealing member 11 of the inner cylinder 3 with the proximal side needle tip.

A lumen part (hollow part) of the double ended needle 71 communicates with the inner cylinder 3 in a state where the sealing member 11 of the inner cylinder 3 is pierced with the proximal side needle tip. The lumen part functions as a flow path through which a liquid from the inner cylinder 3 passes.

The sealing member 11 of the inner cylinder 3 is pierced with the proximal side needle tip and the liquid is injected into the living body through the flow path of the double ended needle 71 after the living body is punctured to a predetermined depth from the skin using the distal side needle tip of the double ended needle 71.

Note that the constituent materials of the double ended needle 71 are not particularly limited, and examples thereof include metallic materials such as stainless steel, aluminum or aluminum alloys, and titanium or titanium alloys.

The double ended needle 71 having such a configuration is mounted in the distal portion of the outer cylinder 4 (cylindrical body 2), that is, in the decreased diameter portion 42b through the support member 72 so as to be movable along the axial direction of the outer cylinder 4. The support member 72 supports the double ended needle 71 with respect to the outer cylinder 4 so as to be movable along the axial direction thereof. The support member 72 forms a bottomed cylindrical shape. The double ended needle 71 is supported and fixed by the bottom part of the support member 72 in a middle part of the double ended needle.

Figure 8:
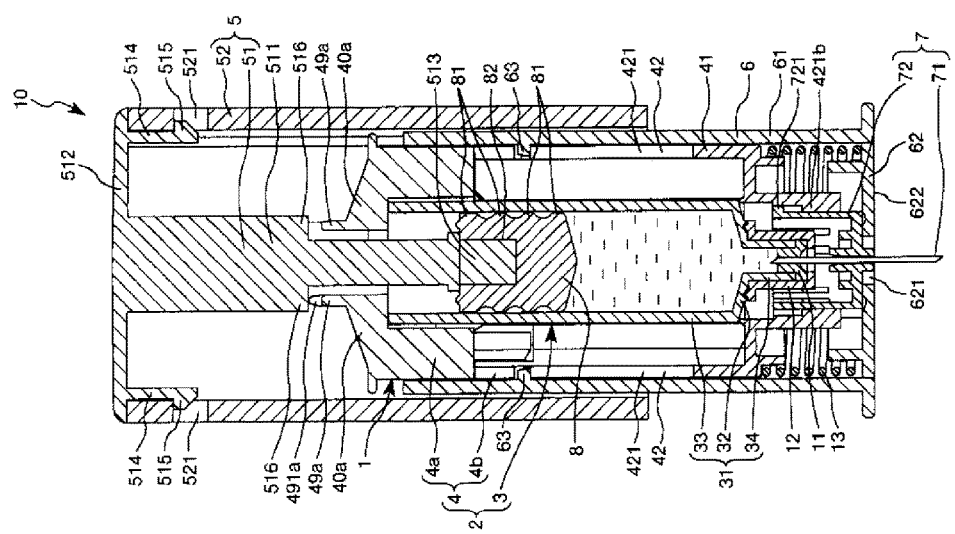
FIG. 8 is a longitudinal sectional view showing the operation state in use of the liquid administration device shown in FIG. 1 in order, when the cover member is in the second position.

In addition, four spurs 721 are arranged in the proximal portion of the support member 72 at equiangular intervals in parallel along the circumferential direction (refer to FIGS. 8 and 10). In addition, one or a plurality of long holes (not shown) that extend in the axial direction of the support member 72 and open in the proximal direction are formed between adjacent spurs 721 of the support member 72. Accordingly, it is possible to decrease or enlarge the diameter of the support member 72 on the proximal side by elastic deformation.

Note that removal of the puncture needle 7 from the distal portion of the cylindrical body 2 is prevented by each spur 721 being engaged with the stepped portion 421b of the decreased diameter portion 42b on the distal side of the outer cylinder 4.

In addition, as shown in FIG. 2, in an unused state (initial state), the puncture needle 7 can be prevented from rotationally moving in the circumferential direction during the puncturing using each spur 721 being disposed in each groove 422b of the decreased diameter portion 42b on the distal side of the outer cylinder 4 and being engaged with the groove 422b. Accordingly, it is possible to prevent coring when the proximal side needle tip of the double ended needle 71 penetrates the sealing member 11.

As mentioned above, the puncture needle 7 is supported so as to be movable to the outer cylinder 4 along the axial direction thereof through the support member 72. Accordingly, the puncture needle 7 can be in a separation state where the proximal side needle tip of the double ended needle 71 is separated from the sealing member 11 of the cylindrical body 2 as shown in FIG. 2, and the puncture needle 7 can be in a pierced state where the sealing member 11 is pierced with the proximal side needle tip of the double ended needle 71 as shown in FIGS. 8 and 10. Accordingly, unintentional leaking of a liquid from the double ended needle 71 is prevented until the puncture needle 7 enters the pierced state.

As shown in FIGS. 2 and 5, the cover member 6 is disposed on the outer peripheral side of the outer cylinder 4 (cylindrical body 2).

The cover member 6 is supported so as to be movable relative to the outer cylinder 4 (cylindrical body 2) along the axial direction thereof similarly to the puncture needle 7. Accordingly, a living body is punctured to a predetermined depth from the skin using the distal side needle tip of the double ended needle 71 after the distal surface 622 of the cover member 6 is brought into contact with the living body.

The cover member 6 has five steps (positions) to be described later from before use to after use. The five positions include a first position (position (A)) (refer to FIGS. 1 and 2) at which the cover member 6 protrudes further on the distal side than the distal side needle tip of the double ended needle 71 in a state before use; a second position (refer to FIGS. 7 and 8) at which the cover member 6 is retreated in the proximal direction from the first position, and the outer cylinder 4 is rotated with respect to the cover member 6 and the inner cylinder 3; a third position (refer to FIGS. 9 and 10) at which the outer cylinder 4 is rotated with respect to the cover member 6 and the inner cylinder 3 at a predetermined angle; a fourth position (FIGS. 11 and 12) at which the distal portion of the operation member 5 reaches the distal portion of the cover member 6 and the administration is completed; and a fifth position (refer to FIGS. 13 to 15) at which the cover member 6 moves in the distal direction from the fourth position (third position) and protrudes further on the distal side than the distal side needle tip of the double ended needle 71, and a safety mechanism is operated after the completion of the administration.

Note that, in the present embodiment, when the cover member 6 is at the first position, the distal surface 622 of the cover member 6 protrudes further on the distal side than the distal side needle tip of the double ended needle 71 to cover the distal side needle tip of the double ended needle 71 using the cover member 6. Accordingly, the distal side needle tip of the double ended needle 71 is not exposed until the cover member 6 moves to the proximal side from the first position, and therefore, it is possible to prevent a user from erroneously puncturing the skin with the distal side needle tip of the double ended needle 71 before the puncturing or to prevent the distal side needle tip from being damaged. In addition, when the cover member 6 is positioned at the second to fourth positions (position (B)), the distal side needle tip of the double ended needle 71 is exposed from the distal end of the cover member 6.

Note that, when the cover member 6 is at the first position, the aforementioned puncture needle 7 enters the separation state where the puncture needle is positioned further on the proximal side than the distal portion of the cover member 6. In contrast, when the cover member 6 moves to the second position, the cover member 6 presses and moves the double ended needle 71 (the double ended needle 71 together with the support member 72) toward the proximal direction, and the proximal side needle tip of the double ended needle 71 pierces the sealing member 11 of the cylindrical body 2 and the distal side needle tip of the double ended needle 71 punctures a living body. However, when the cover member 6 is at the second position, the piercing of the sealing member 11 with the distal side needle tip of the double ended needle 71 is not completed, and the upper end surface inside the support member 72 and the distal surface of the decreased diameter portion 42b of the distal side member 4b of the outer cylinder 4 are in a state of being slightly separated from each other. Then, the piercing of the sealing member 11 with the proximal side needle tip of the double ended needle 71 is completed at the third position at which the outer cylinder 4 is rotated with respect to the cover member 6 and the inner cylinder 3, and the upper end surface inside the support member 72 and the distal surface of the decreased diameter portion 42b of the distal side member 4b of the outer cylinder 4 enter a state of being brought into contact with each other.

The cover member 6 is configured to have a plate-shaped distal end wall part 62 that is disposed in the distal portion; and a side wall 61 that is erected in the proximal direction from the distal end wall part 62, that is, a member with a bottomed cylindrical shape. In addition, the cover member 6 has a distal surface 622 at the distal end.

An opening portion 621 penetrating a central portion is formed in the central portion of the distal end wall part 62. As shown in FIGS. 6 to 9, when the cover member 6 is at the second to fourth positions, the distal side needle tip of the double ended needle 71 protrudes (is exposed) from the opening portion 621.

As shown in FIG. 5, the side wall 61 forms a cylindrical shape. A pair of ribs 614 that protrudes outward is formed on the outer peripheral surface of the proximal portion of the side wall 61. The ribs 614 are disposed so as to face each other. Each rib 614 extends in the axial direction of the cover member 6.

In addition, a pair of elastic arm portions 612 is protrusively formed in the middle of the side wall 61 in the proximal direction, and a spur 613 which protrudes inward is formed in the proximal portion of each of the arm portions 612. The arm portions 612 are disposed so as to face each other Each spur 613 is disposed further on the distal side than the proximal end of the side wall 61. Note that the arm portions 612, spurs 613, and the ribs 614 are respectively arranged at substantially equiangular intervals along the circumferential direction of the cover member 6 when seen from the axial direction of the cover member 6.

In addition, a pair of spurs 63 that protrudes inward is formed on the inner peripheral surface of the proximal portion of the side wall 61 (refer to FIG. 1). The spurs 63 are disposed so as to face each other The spurs 63 are disposed in the cam grooves 42 of the outer cylinder 4, that is, engaged with each cam groove 42. The relationship between the spur 63 and each cam groove 42 of the outer cylinder 4 in a series of operation will be described later.

In an unused state (initial state), the spurs 613 of the cover member 6 are disposed in the long holes 43b of the outer cylinder 4. When the cover member 6 moves in the axial direction of the outer cylinder 4, and when the outer cylinder 4 is rotated with respect to the cover member 6 at a predetermined angle by the cam groove 42 of the outer cylinder 4 and the spur 63 of the cover member 6, the spurs 613 of the cover member 6 moves to the surface on the proximal side of the body section 41 of the long holes 44b of the outer cylinder 4.

As shown in FIG. 2, a coil spring (compression coil spring) 13 is stored in the cover member 6 in a compressed state. The distal portion of the coil spring 13 abuts on the distal end wall part 62 inside the cover member 6, and the proximal portion of the coil spring 13 abuts on the inside of the body section 41 of the outer cylinder 4 on the distal side. In the compressed state of the unused state, the coil spring 13 is compressed by the weight loaded on the distal end of the outer cylinder 4. Note that the coil spring 13 may not be compressed if the distal portion of the coil spring 13 abuts on the distal end wall part 62 inside the cover member 6 and the proximal portion of the coil spring 13 abuts on the inside of the body section 41 of the outer cylinder 4 on the distal side. For example, it is possible to bias the cover member 6 from the second position toward the first position (toward the distal direction) using the coil spring 13. With the biasing force of such a coil spring 13, the distal surface 622 of the cover member 6 can be made to protrude further on the distal side than the distal side needle tip of the double ended needle 71 until the liquid administration device 10 is used, and accordingly, it is possible to reliably prevent the erroneous puncturing due to the distal side needle tip.

Note that the constituent materials of the coil spring 13 are not particularly limited, and for example, metallic materials such as stainless steel and copper can be used.

The gasket 8 is stored in the inner cylinder 3 (cylindrical body 2) so as to be slidable along the axial direction of the inner cylinder 3. Note that the space surrounded by the gasket 8 and the inner cylinder 3 is filled with a liquid in advance. The liquid in the inner cylinder 3 can be pushed out from the double ended needle 71 in a state of communicating with the inner cylinder 3 due to the gasket 8 moving toward the distal direction.

The outer shape of the gasket 8 is a columnar shape, and four protruded parts 81 are formed in the outer peripheral part. Adjacent protruded parts 81 are separated along the axial direction of the gasket 8. In addition, each of the protruded parts 81 forms a ring shape along the circumferential direction of the gasket 8, and the outer diameter thereof is slightly larger than the inner diameter of the inner cylinder 3 in a natural state where external force is not applied. Accordingly, each of the protruded parts 81 can slide while being brought into close contact with the inner peripheral part of the side wall 33 of the inner cylinder 3, and thus, it is possible to reliably retain the liquid-tightness and improve slidability.

In addition, a recess portion 82, which interlocks a main body portion 511 of a plunger 51 of the operation member 5 by inserting (fitting) the main body portion therein, is opened on the proximal surface of the gasket 8.

As shown in FIG. 1, the operation member 5 has the plunger 51 that interlocks with the gasket 8 on the proximal side of the gasket 8 and presses the gasket 8 in the distal direction; and an outermost cylinder (outer cylinder) (grip portion) 52. The plunger 51 and the outermost cylinder 52 are interlocked with each other. The operation member 5 is a member that performs a pressing operation (discharging operation) to discharge a liquid in the inner cylinder 3 from the double ended needle 71 by moving the gasket 8 in the distal direction using the plunger 51.

As shown in FIGS. 2 and 6, the plunger 51 has a bar-shaped main body portion 511 whose transverse cross section is, for example, a cross-shape or a circular-shape, and the gasket 8 is fixed to the distal end of the main body portion 511. A disk-shaped flange 512 is formed at the proximal end of the main body portion 511.

An interlock portion 513 that corresponds to the shape of the recess portion 82 of the gasket 8 is formed in the distal portion of the main body portion 511. The plunger 51 (operation member 5) and the gasket 8 are interlocked with each other by the interlock portion 513 being disposed in the recess portion 82 of the gasket 8. Note that the method of fixing the gasket 8 to the main body portion 511 is not particularly limited thereto, and other examples thereof include a method of forming a male screw on the main body portion 511, forming a female screw, which is configured to be screwed into the male screw, on the gasket 8, and screwing both the screws together. Note that, in the present example, the operation member 5 is interlocked to the gasket 8 on the proximal side, but the operation member may not be interlocked therewith.

In addition, a pair of elastic arm portions 514 is protrusively formed on the proximal surface of the flange 512 of the plunger 51 in the distal direction, and a claw 515 that protrudes outward is formed in the distal portion of each of the arm portions 514. The elastic arm portions 514 are disposed so as to face each other.

The plunger 51 has a plate-shaped part that forms an elongated shape and has a pair of stepped portions 516 in which the width of the plate-shaped part is changed; the pair of stepped portions 516 is the first engagement portion that can be engaged with a pair of spurs (second engagement portion) 49a. That is, a pair of stepped portions (first engagement portion) 516 is formed on the distal side of the main body portion 511 of the plunger 51. The stepped portions 516 are disposed so as to face each other. With the stepped portions 516 and the spurs 49a, an engagement mechanism (engagement portion) is constituted in which the engagement portion enters an engagement state where the pressing operation is inhibited when the stepped portions 516 and the spurs 49a are engaged with each other, and enters a released state where the pressing operation can be performed when the engagement state is released.

Note that the number of stepped portions (first engagement portions) 516 is not limited to two, and examples thereof may include one or three or greater.

In addition, the stepped portion (first engagement portion) may be formed in the inner structure 1 and the spur (second engagement portion) may be formed in the operation member 5.

In an unused (initial) state, each of the stepped portions 516 of the plunger 51 is at a position at which each of the stepped portions is engaged or can be engaged with each of the spurs 49a of the outer cylinder 4, and accordingly, the movement of the plunger 51 to the cylindrical body 2 in the distal direction is inhibited. When the cover member 6 moves in the axial direction of the outer cylinder 4 and the outer cylinder 4 moves to a position at which the outer cylinder can be rotated with respect to the cover member 6 at a predetermined angle by the cam groove 42 of the outer cylinder 4 and the spur 63 of the cover member 6, each of the stepped portions 516 of the plunger 51 moves to a position that is deviated from each of the spurs 49a of the outer cylinder 4, and each of the stepped portions 516 and each of the spurs 49a are disengaged. As a result, the plunger 51 can move to the cylindrical body 2 in the distal direction.

The outermost cylinder 52 is disposed on the outer peripheral side of the inner structure 1 and the cover member 6. The outermost cylinder 52 forms a cylindrical shape and functions as the grip portion when gripping the operation member 5.

In addition, a pair of hole portions 521 is formed in the proximal portion of the outermost cylinder 52. The hole portions 521 are disposed so as to face each other The claws 515 of the plunger 51 are disposed in the hole portions 521 from the inside of the outermost cylinder 52, and the claws 515 and the hole portions 521 are engaged with each other. As a result, the outermost cylinder 52 and the plunger 51 are interlocked with each other.

An auxiliary mechanism 40 has a function of generating auxiliary force for pressing the gasket 8 through the plunger 51 of the operation member 5. In the present embodiment, the auxiliary mechanism 40 is constituted by a pair of coil springs (extension coil springs: second biasing members) 401. The proximal portion of each of the coil springs 401 is fixed to the proximal portion of the plunger 51, and the distal portion of each of the coil springs 401 is fixed to the proximal side member 4a of the outer cylinder 4, in an extended state. Accordingly, each of the coil springs 401 biases the inner structure 1 and the operation member 5 in a direction approaching each other. That is, each of the coil springs 401 generates auxiliary force for pressing the gasket 8 in the distal direction through the plunger 51 of the operation member 5. Accordingly, it is possible to easily move the operation member 5 in the distal direction.

Note that the constituent material of the coil spring 401 is not particularly limited, and for example, it is possible to use the same material as that of the constituent material of the coil spring 13.

In addition, a pair of grooves (not shown) is formed on the inner peripheral surface of the outermost cylinder 52. The pair of groves are disposed so as to face each other. Each of the grooves extends along the axial direction of the outermost cylinder 52. The ribs 614 of the cover member 6 are disposed in the grooves. Accordingly, the rotation of the cover member 6 with respect to the outermost cylinder 52 is prevented.

Next, the usage of the liquid administration device 10 and the operation state when in use will be described with reference to FIGS. 1, 2, and 7 to 15.

As shown in FIGS. 1 and 2, the liquid administration device 10 in an unused state (initial state) is prepared. In the liquid administration device 10 in the unused state, the cover member 6 is at the first position and covers the distal side needle tip of the double ended needle 71. Note that, in the unused state, the distal side needle tip of the double ended needle 71 is maintained in a state of being covered with the cover member 6 due to the biasing force of the coil spring 13. Accordingly, erroneous puncturing due to the distal side needle tip of the double ended needle 71 can be reliably prevented.

In addition, in the puncture needle 7, the proximal side needle tip of the double ended needle 71 is separated from the sealing member 11 of the inner cylinder 3 of the cylindrical body 2, and does not pierce the sealing member 11 yet. Accordingly, it is possible to maintain the liquid in an aseptic state until administration of the drug solution starts.

In addition, each of the spurs 63 of the cover member 6 is positioned at a position shown in FIG. 1 with respect to the outer cylinder 4.

In addition, each of the spurs 613 of the cover member 6 is positioned on the proximal side of the long holes 43b of the distal portion of the outer cylinder 4.

In addition, each of the stepped portions 516 of the plunger 51 is at a position at which each of the stepped portions abuts or can abut (may be separated before use) on the slope 491a of each of the spurs 49a of the outer cylinder 4, that is, at a position at which each of the stepped portions is engaged or can be engaged with each of the spurs 49a. As a result, the movement of the operation member 5 to the inner structure 1 (cylindrical body 2) in the distal direction is inhibited.

In addition, the spur 63 is disposed in the linear groove 421, and accordingly, the outer cylinder 4 is inhibited from being rotated with respect to the cover member 6. As a result, the outer cylinder 4 is inhibited from being rotated with respect to the operation member 5.

Figure 7:
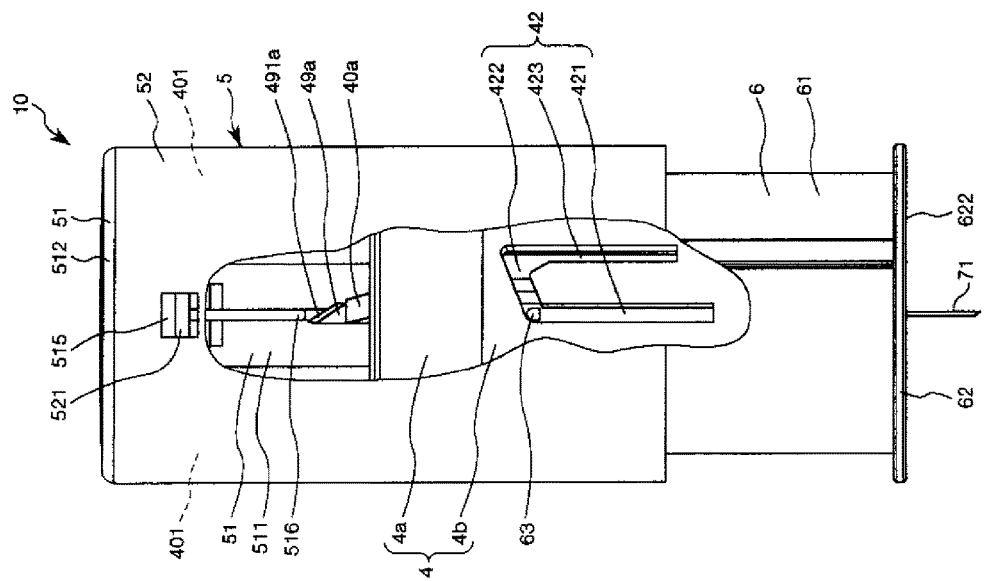
FIG. 7 is a side view showing an operation state in use of the liquid administration device shown in FIG. 1 in order, when the cover member is in a second position.

Next, as shown in FIGS. 7 and 8, the operation member 5 of the liquid administration device 10 in the unused state is gripped, the distal end wall part 62 of the cover member 6 is abutted on a living body, and the operation member 5 is pressed toward the distal direction. Accordingly, the cover member 6 moves to the operation member 5 and the inner structure 1 in the proximal direction, that is, from the first position to the second position against the biasing force of the coil spring 13. In addition, in the moving process, the distal end wall part 62 of the cover member 6 moves the support member 72 of the puncture needle 7 to the proximal portion side.

At this time, the distal side needle tip of the double ended needle 71 protrudes from the opening portion 621 of the distal end wall part 62 of the cover member 6, and the living body is punctured with the distal side needle tip. In addition, the distal end wall part 62 presses the support member 72 of the puncture needle 7 toward the proximal direction. Accordingly, it is possible to pierce the sealing member 11 of the inner cylinder 3 with the proximal side needle tip of the double ended needle 71, and thus, the double ended needle 71 puncturing the living body communicates with the inner cylinder 3.

At this time, the spur 63 of the cover member 6 moves relative to the outer cylinder 4 in the proximal direction along the linear groove 421. When the cover member 6 is at the second position, the spur 63 of the cover member 6 is positioned as shown in FIG. 7 with respect to the outer cylinder 4.

In addition, each of the spurs 613 of the cover member 6 at this time is in a state where each of the spurs moves in the proximal direction along the long holes 43b of the outer cylinder 4, runs on the body section 41 of the outer cylinder 4 while bending each of the spurs 613 of the cover member 6 (outward from the central axis) from the proximal portion of each of the long holes 43b, and further moves to the proximal side.

In addition, the spur 63 is positioned in the proximal portion of the linear groove 421, and accordingly, the outer cylinder 4 can be rotated with respect to the cover member 6. As a result, the outer cylinder 4 can be rotated with respect to the operation member 5.

Figure 9:
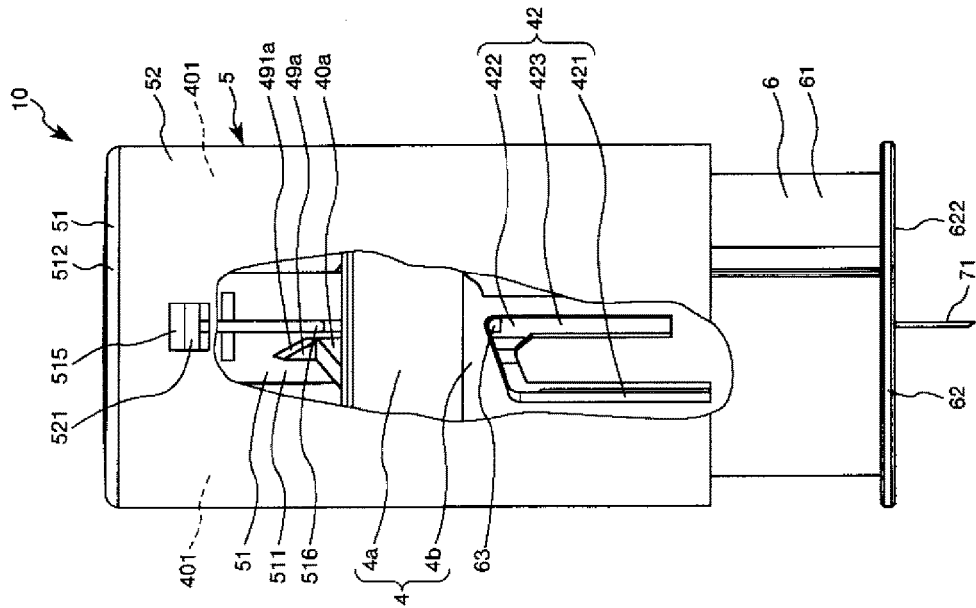
FIG. 9 is a side view showing the operation state in use of the liquid administration device shown in FIG. 1 in order, when the cover member is in a third position.

Next, when the operation member 5 is continuously pressed in the distal direction in the state shown in FIGS. 7 and 8, the cover member 6 reaches the third position as shown in FIGS. 9 and 10. This state is a state in which the rotation of the outer cylinder 4 with respect to the cover member 6 and the inner cylinder 3 at a predetermined angle due to the cam groove 42 of the outer cylinder 4 and the spur 63 of the cover member 6 has been finished.

At this time, the stepped portion 516 of the plunger 51 moves along the slope 491a of the spur 49a, and at this time, the outer cylinder 4 obtains propulsive force in the rotational direction. Accordingly, it is possible to easily rotate the outer cylinder 4.

Accordingly, each of the stepped portions 516 of the plunger 51 moves to a position of being deviated from each of the spurs 49a of the outer cylinder 4 and enters a state where each of the stepped portions 516 and each of the spurs 49a are disengaged. Accordingly, the operation member 5 can move to the cylindrical body 2 in the distal direction. After that, the state where each of the stepped portions 516 and each of the spurs 49a are disengaged is maintained, and therefore, the description thereafter will not be repeated.

Note that the operation of puncturing a living body with the double ended needle 71, the rotational operation of the outer cylinder 4, and the pressing operation of the operation member 5 to be described later can be smoothly performed as a continuous operation.

In addition, the spur 63 of the cover member 6 moves relative to the outer cylinder 4 along the inclined groove 422 in an oblique upward direction. Then, when the cover member 6 is in the third position, the spur 63 of the cover member 6 is positioned at the position shown in FIG. 9 with respect to the outer cylinder 4.

In addition, at this time, each of the spurs 613 of the cover member 6 rotates while maintaining a state where each of the spurs 613 of the cover member 6 is bent (outward from the central axis) and enters a state where each of the spurs is moved onto the surface of the body section 41 of each of the long holes 44b on the proximal portion side.

Figure 11:
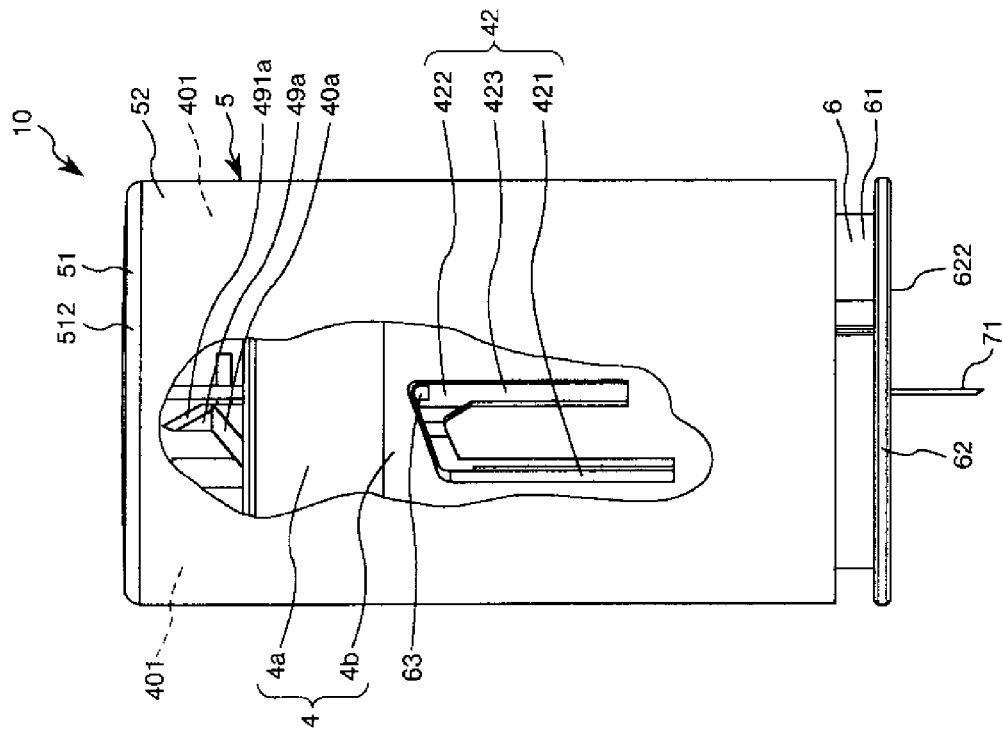
FIG. 11 is a side view showing the operation state in use of the liquid administration device shown in FIG. 1 in order, when the cover member is in a fourth position.
Figure 12:
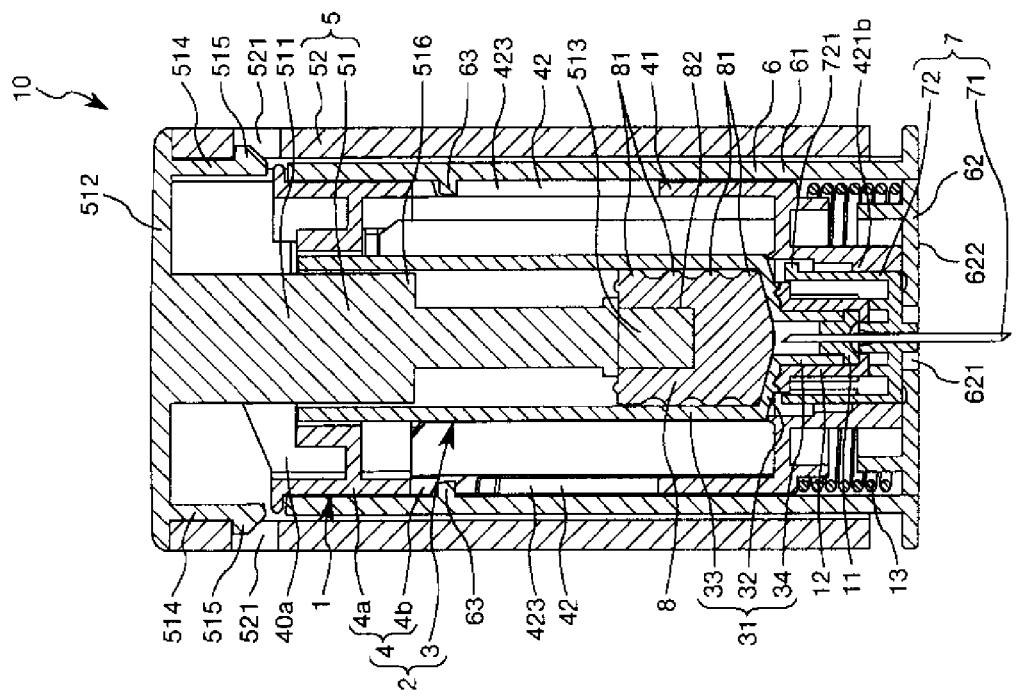
FIG. 12 is a longitudinal sectional view showing the operation state in use of the liquid administration device shown in FIG. 1 in order, when the cover member is in the fourth position.

As shown in FIGS. 9 and 10, the operation member 5 moves in the distal direction using the biasing force of the coil spring 401, that is, the auxiliary force thereof in the state where the cover member 6 is positioned at the third position, and accordingly, the gasket 8 can move toward the distal direction. That is, the aforementioned pressing operation is performed, and therefore, it is possible to perform administration of a liquid. As shown in FIGS. 11 and 12, the gasket 8 abuts on the bottom part 32 of the inner cylinder 3, the administration of a liquid is completed, and the cover member 6 is positioned at the fourth position.

At this time, the spur 63 of the cover member 6 is maintained at the position shown in FIG. 11 with respect to the outer cylinder 4.

Furthermore, each of the spurs 613 of the cover member 6 is also maintained at the position on the surface of the body section 41 of each of the long holes 44b on the proximal portion side in a state where each of the spurs 613 of the cover member 6 is bent (outward from the central axis).

Figure 13:
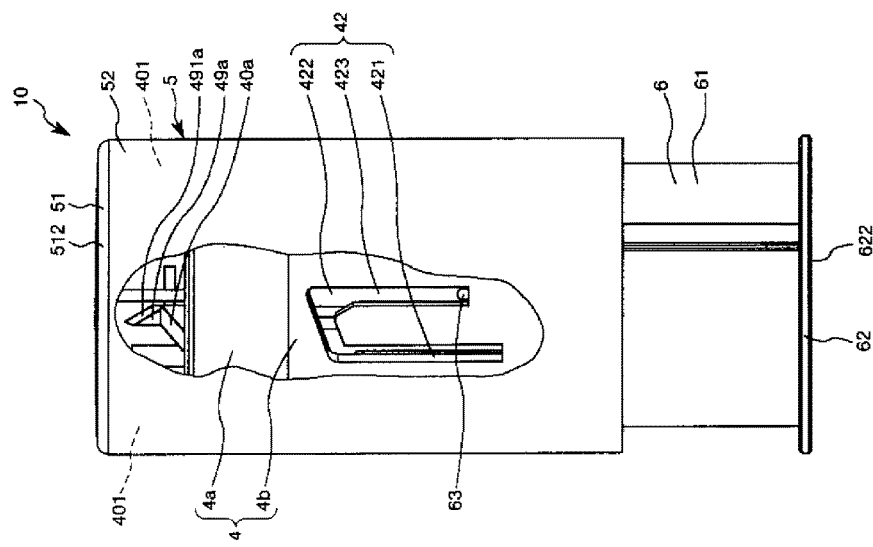
FIG. 13 is a side view showing the operation state in use of the liquid administration device shown in FIG. 1 in order, when the cover member is in a fifth position.
Figure 14:
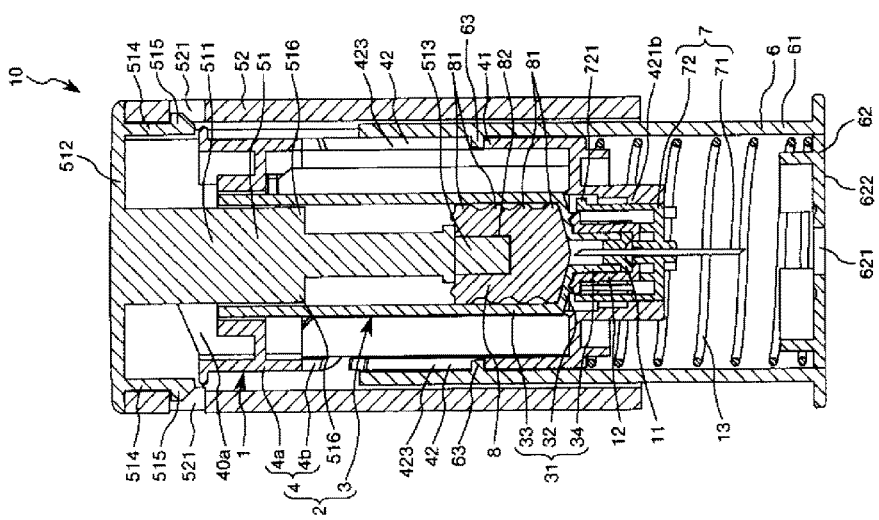
FIG. 14 is a longitudinal sectional view showing the operation state in use of the liquid administration device shown in FIG. 1 in order, when the cover member in in the fifth position.
Figure 15:
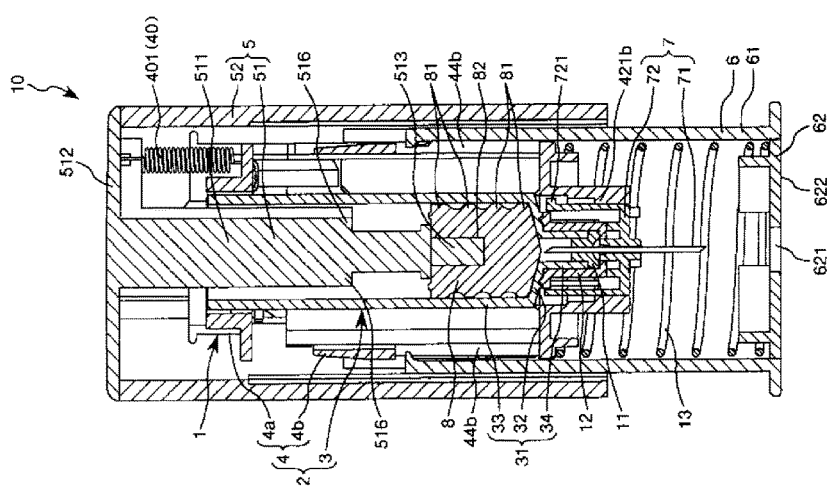
FIG. 15 is a second longitudinal sectional view showing the operation state in use of the liquid administration device shown in FIG. 1 in order, when the cover member in in the fifth position.

Next, as shown in FIGS. 13 to 15, the pressing of the operation member 5 toward the distal direction is stopped, the distal end wall part 62 of the cover member 6 is separated from a living body, and the double ended needle 71 is removed from the living body.

Accordingly, the cover member 6 moves in the distal direction, that is, to the fifth position using the biasing force of the coil spring 13, and the distal side needle tip of the double ended needle 71 is covered with the cover member.

In addition, the cover member 6 is inhibited from moving to the outer cylinder 4 in the proximal direction by each of the spurs 613 of the cover member 6 being engaged with the proximal portion of the long hole 44b. As a result, the state where the distal side needle tip of the double ended needle 71 is covered with the cover member 6 is maintained. Accordingly, the cover member 6 cannot move in the proximal direction, and therefore, functions as a safety mechanism which prevents needle piercing accidents after use.

In addition, with the relative rotation of the outer cylinder 4 with respect to the cover member 6, each of the spurs 613 of the cover member 6 is engaged with the long hole 44b from the long hole 43b (initial state) of the outer cylinder 4, and the state of the device is less likely to return to its initial state compared to a straight advance type device through the function of the safety mechanism and the state before and after use can be easily recognized, and therefore, it is possible to prevent reuse of the device. Furthermore, it is possible to safely and reliably dispose of the used liquid administration device 10 without mistaking the used device for a liquid administration device 10 before use.

In addition, the spur 63 of the cover member 6 moves relative to the cover member 6 along the linear groove 423 in the distal direction, and when the cover member 6 is at the fifth position, the spur 63 of the cover member 6 is positioned at the position shown in FIG. 13 with respect to the outer cylinder 4.

As described above, according to the liquid administration device 10, the stepped portion 516 and the spur 49a which are in the engagement state are made to relatively rotate around the central axis of the inner structure 1 to be set to the released state. Therefore, the direction of relative displacement of the stepped portion 516 and the spur 49a when making them enter the released state is different from the direction of the pressing operation of the operation member 5. Accordingly, it is possible to prevent the stepped portion 516 and the spur 49a from unintentionally entering the released state and to prevent a liquid from unintentionally leaking from the double ended needle 71 before or in the middle of puncturing of the skin with the double ended needle 71.

In addition, the operation of puncturing a living body with the double ended needle 71, the rotational operation of the outer cylinder 4, and the pressing operation of the operation member 5 can be smoothly performed as a continuous operation.

In addition, when being set to the released state, the outer cylinder 4 obtains propulsive force in the rotational direction using the slope 491a, and accordingly, it is possible to easily rotate the outer cylinder 4.

In addition, it is possible to support the movement of the operation member 5 in the distal direction or to move the operation member 5 in the distal direction using the biasing force of the coil spring 401, that is, the auxiliary force thereof.

Accordingly, it is possible to easily and reliably administer a liquid by dispersing more force in a gravitational direction into force in a rotational direction compared to the straight advance type device in which only force in the gravitational direction is exerted, even for users who have difficulty in performing the pressing operation of the operation member 5, for example, an elderly person, a female, or the like with a weak amount of force, and a patient with rheumatism who has a pain or deformation in the fingers.

Note that, in the present embodiment, the puncture needle has the needle tube as the double ended needle, but the present invention is not limited thereto, and the puncture needle may have a needle tube without a needle tip on a proximal side. In this case, the needle tube communicates with the inner cylinder in advance (already in an unused state).

Second Embodiment

Figure 16:
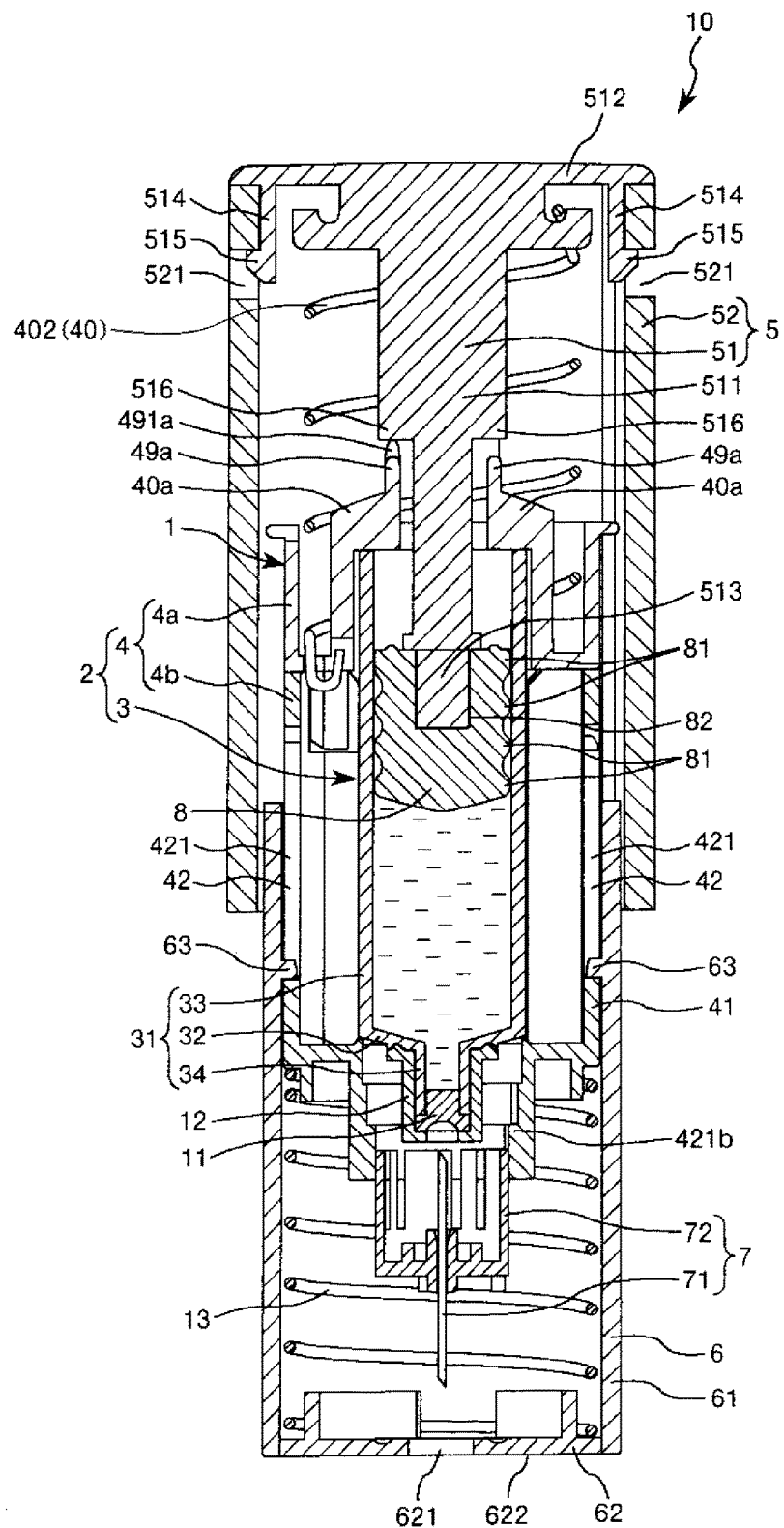
FIG. 16 is a longitudinal sectional view showing a second embodiment of a liquid administration device of the present invention.

FIG. 16 is a longitudinal sectional view showing a second embodiment of a liquid administration device of the present invention. Note that, hereinafter, the upper side is described as "proximal end (rear end)" or "upper (upward)", the lower side is described as "distal end" or "lower (downward), and the vertical direction is described as "axial direction" or "longitudinal direction" in FIG. 16.

Hereinafter, in regard to the second embodiment, the difference between the second embodiment and the aforementioned first embodiment will be mainly described, and the description of the same matter will not be repeated.

As shown in FIG. 16, in the liquid administration device 10 of the second embodiment, an auxiliary mechanism 40 has one coil spring (second biasing member) 402. The coil spring 402 also serves as a third biasing member which biases one of a stepped portion (first engagement portion) 516 and a spur 49a (second engagement portion) to the other in a rotational direction of an inner structure 1 around a central axis. That is, the coil spring 402 is installed in a state of being twisted in an unused state (initial state), and an outer cylinder 4 is biased to an operation member 5 in a direction in which the outer cylinder is rotated, that is, in a direction in which the outer cylinder is rotated such that the states of the engagement portions enter a released state from an engagement state. With such a coil spring 402, it is possible to more easily rotate the outer cylinder 4 with respect to the operation member 5.

Note that the coil spring 402 also serves as a third biasing member which biases one of the stepped portion (first engagement portion) 516 and the spur 49a (second engagement portion) to the other in a rotational direction of the inner structure 1 around the central axis.

According to the liquid administration device 10, the same effect as that in the aforementioned first embodiment can be obtained.

Third Embodiment

Figure 17:
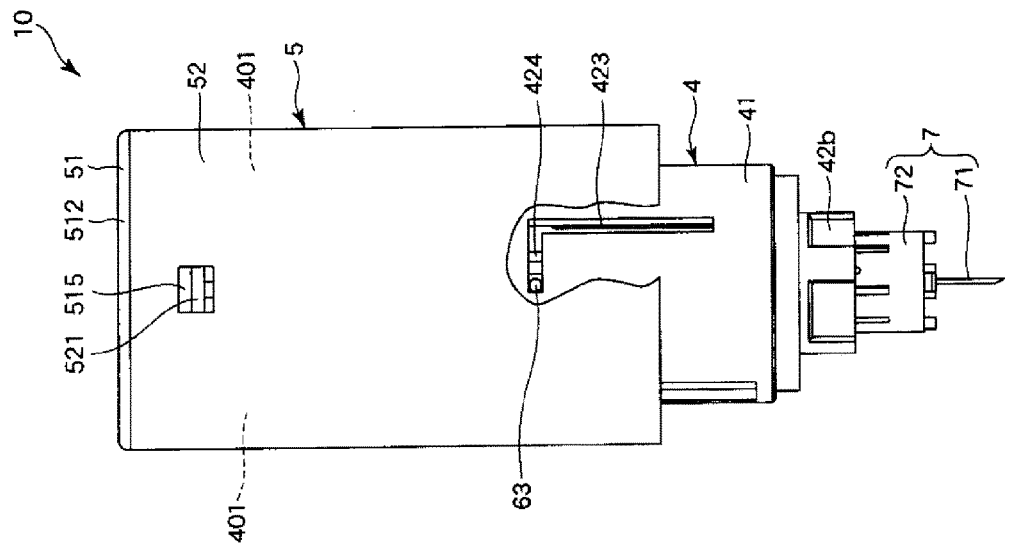
FIG. 17 is a side view showing a third embodiment of a liquid administration device of the present invention in an initial state.
Figure 18:
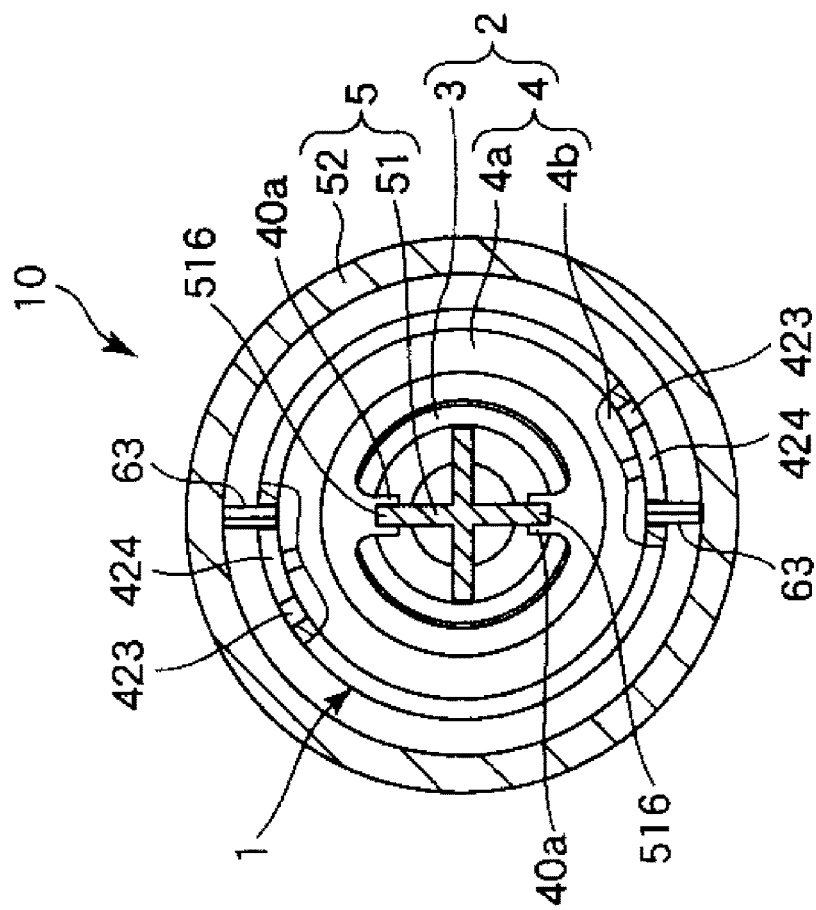
FIG. 18 is a transverse cross-sectional view of the liquid administration device shown in FIG. 17.
Figure 19:
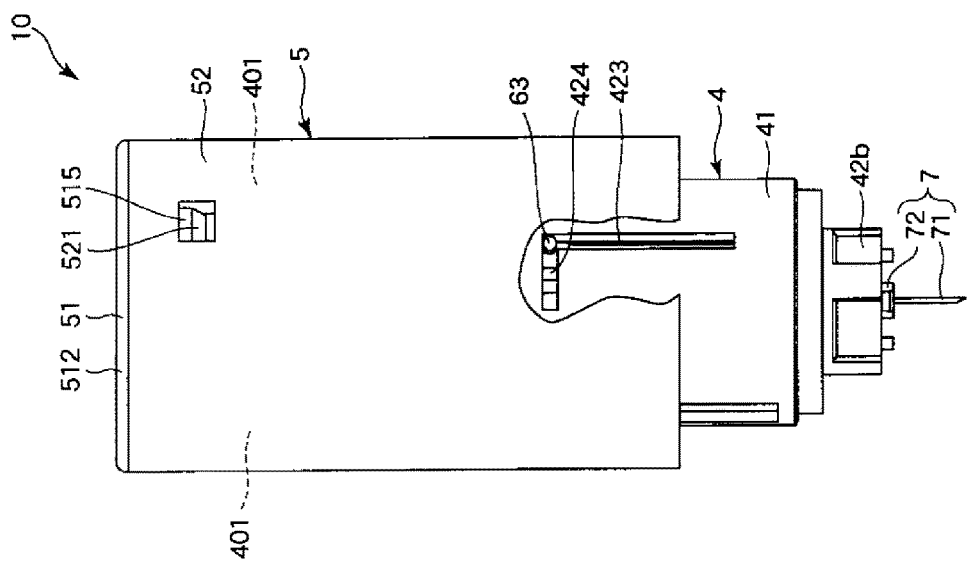
FIG. 19 is a side view showing the third embodiment of the liquid administration device of the present invention in a state during use.
Figure 20:
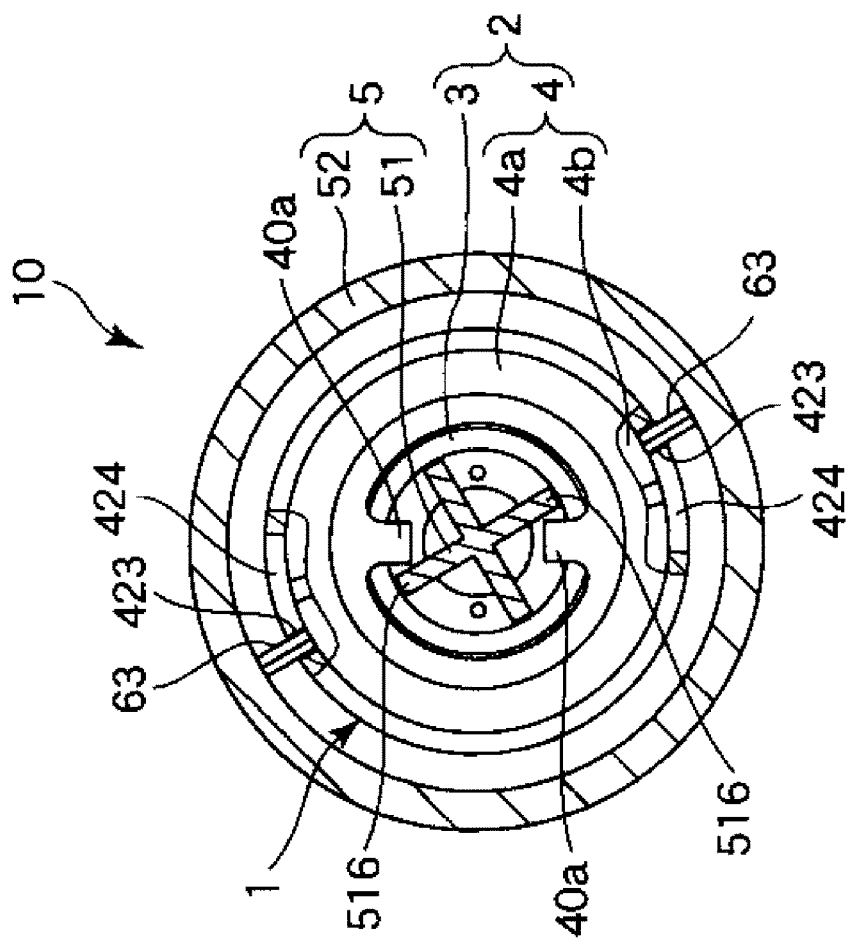
FIG. 20 is a transverse cross-sectional view of the liquid administration device shown in FIG. 19.

FIGS. 17 and 19 are respectively side views showing a third embodiment of a liquid administration device of the present invention. FIGS. 18 and 20 are transverse cross-sectional views of the liquid administration device shown in FIGS. 17 and 19. Note that, hereinafter, the upper side is described as "proximal end (rear end)" or "upper (upward)", the lower side is described as "distal end" or "lower (downward), and the vertical direction is described as "axial direction" or "longitudinal direction" in FIGS. 17 to 19.

Hereinafter, in regard to the third embodiment, the difference between the third embodiment and the aforementioned first embodiment will be mainly described, and the description of the same matter will not be repeated.

As shown in the drawings, a cover member 6 is omitted in the liquid administration device 10 of the third embodiment.

In addition, a cam groove 42 is changed to linear grooves 423 and 424. The linear groove 424 is formed on an outer peripheral surface of a body section 41 and extends in a direction perpendicular to the axis of an outer cylinder 4. The linear groove 424 is formed to be shorter than one turn. The linear groove 423 is linearly formed on the outer peripheral surface of the body section 41 and extends in an axial direction of the outer cylinder 4. An end portion of the linear groove 424 on the right side in FIG. 17 and a proximal portion of the linear groove 423 communicate with each other. In addition, a spur 63 is formed on an inner peripheral surface of an outermost cylinder 52.

In addition, a protruding portion 40a of the outer cylinder 4 does not have a spur 49a, and a stepped portion 516 of a plunger 51 is engaged with an end portion (distal portion) of the protruding portion 40a on the central axis side in an engagement state.

As shown in FIGS. 17 and 18, in the liquid administration device 10, in an unused state (initial state), the spur 63 of the cover member 6 is positioned at positions shown in FIGS. 17 and 18 with respect to the outer cylinder 4. In addition, the stepped portion 516 of the plunger 51 is engaged with the end portion of the protruding portion 40a on the central axis side.

As shown in FIGS. 19 and 20, the operation member 5 is rotated with respect to the outer cylinder 4 through manual operation during use. Accordingly, the spur 63 of the cover member 6 moves to positions shown in FIGS. 19 and 20 with respect to the outer cylinder 4. In addition, the engagement between the stepped portion 516 of the plunger 51 and the end portion of the protruding portion 40a on the central axis side is released and enters a released state.

According to the liquid administration device 10, the same effect as that in the aforementioned first embodiment can be obtained.

Fourth Embodiment

Figure 21B:
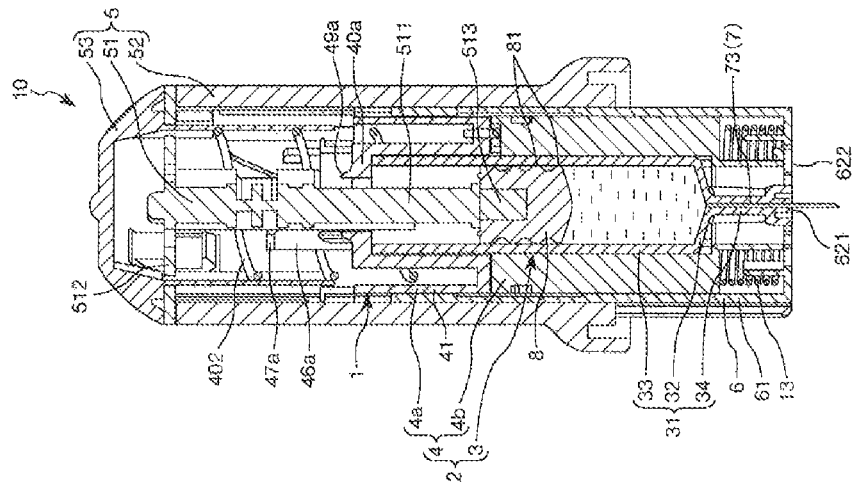
FIG. 21(B) is a longitudinal sectional view showing the fourth embodiment of the liquid administration device of the present invention in a state where a needle tip side cap and a cap are removed.
Figure 21A:
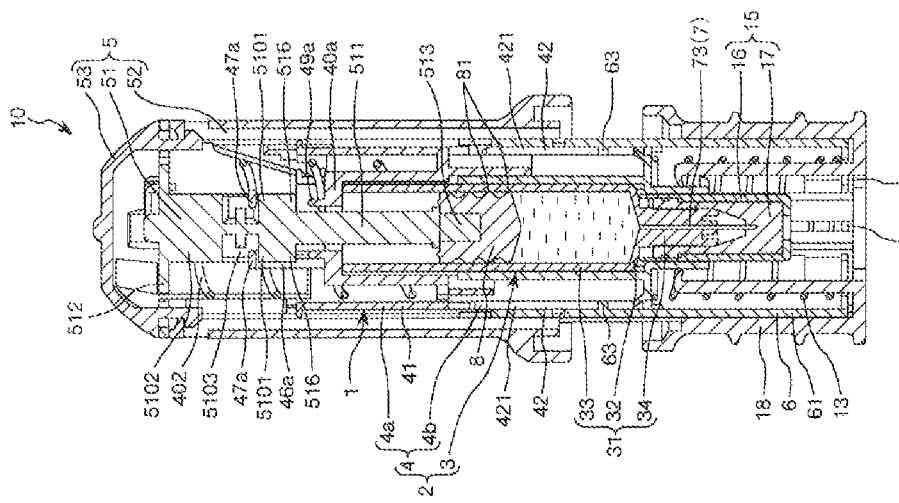
FIG. 21(A) is a longitudinal sectional view showing a fourth embodiment of a liquid administration device of the present invention in an initial state.
Figure 22:
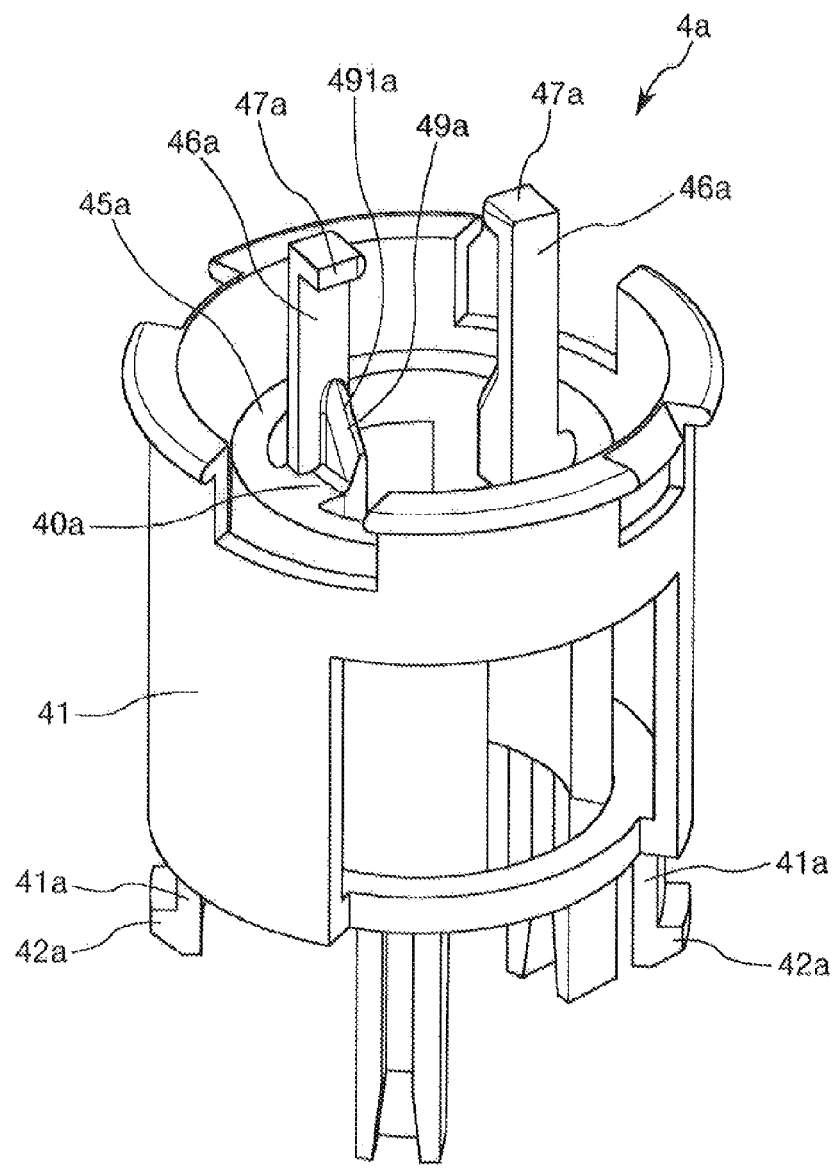
FIG. 22 is a perspective view of a proximal side member of an outer cylinder of a cylindrical body of the liquid administration device shown in FIGS. 21(A) and 21(B).
Figure 23:
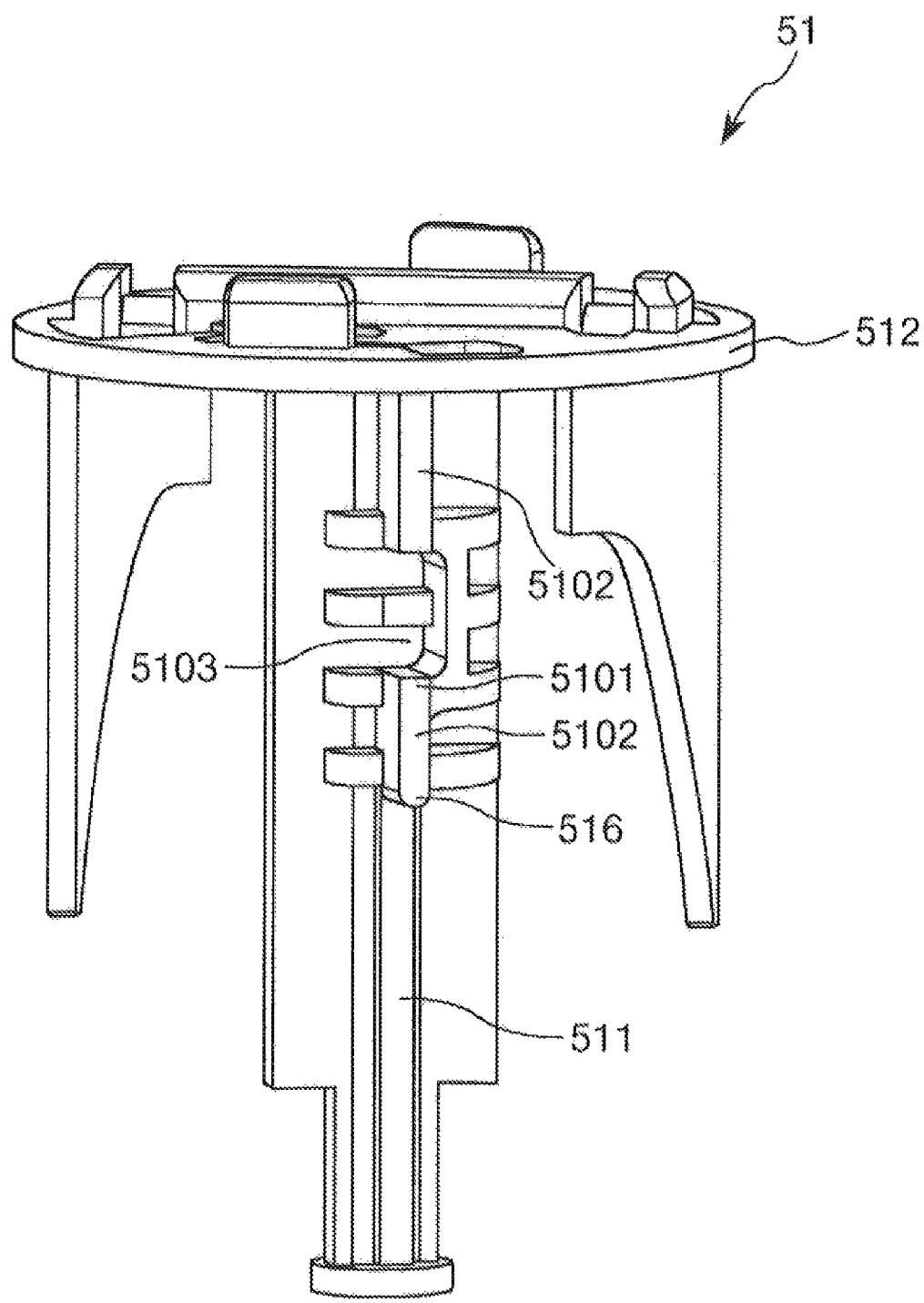
FIG. 23 is a perspective view of a plunger of the liquid administration device shown in FIGS. 21(A) and 21(B).

FIGS. 21(A) and 21(B) are longitudinal sectional views showing a fourth embodiment of a liquid administration device of the present invention. FIG. 22 is a perspective view of a proximal side member of an outer cylinder of a cylindrical body of the liquid administration device shown in FIGS. 21(A) and 21(B). FIG. 23 is a perspective view of a plunger of the liquid administration device shown in FIGS. 21(A) and 21(B). Note that, hereinafter, the upper side is described as "proximal end (rear end)" or "upper (upward)", the lower side is described as "distal end" or "lower (downward), and the vertical direction is described as "axial direction" or "longitudinal direction" in FIGS. 21(A) to 23.

Hereinafter, in regard to the fourth embodiment, the difference between the fourth embodiment and the aforementioned first embodiment will be mainly described, and the description of the same matter will not be repeated.

As shown in these drawings, in the liquid administration device 10 of the fourth embodiment, a puncture needle 7 is configured to have a needle tube 73 which is fixed to an opening part 34 of an inner cylinder 3 and has a sharp needle tip at a distal end.

In addition, the liquid administration device 10 has a cap 18 which is freely detachably mounted on a cover member 6, and a needle tip side cap 15 which is freely detachably mounted on the opening part 34 of the inner cylinder 3. The needle tip side cap 15 is configured to have a bottomed cylindrical shaped housing 16, and an elastic body 17 which is installed on the inner peripheral surface of the housing 16. In a state where the needle tip side cap 15 is installed on the opening part 34 of the inner cylinder 3, the needle tip of the needle tube 73 is protected by being brought into contact with the elastic body 17, and a distal end opening of the needle tube 73 is sealed with an elastic body 17.

In addition, an operation member 5 has a head portion 53, an outermost cylinder 52, and a plunger 51 which are interlocked with each other.

As shown in FIG. 23, a pair of engagement portions 5101 which can be engaged with a pair of claws 47a of a proximal side member 4a of an outer cylinder 4 to be described later is formed in the middle of a main body portion 511 of the plunger 51. The engagement portion 5101 is constituted by the end portion of an elongated plate shaped portion 5102 on the distal side of a cutout portion 5103 which is provided in the middle of the plate shaped portion 5102 extending in the axial direction of the plunger 51, and is set to be able to be engaged with the claw 47a along the axial direction of the plunger 51 and the outer cylinder 4 (refer to FIG. 21(A)). Note that the engagement portion 5101 is disposed on the proximal side of the stepped portion 516.

In addition, as shown in FIG. 22, a pair of elastic arm portions 46a and are disposed so as to face to each other are protrusively formed on the proximal side of a decreased diameter portion 45a of the proximal side member 4a of the outer cylinder 4 in the proximal direction. Distal portions of the arm portions 46a are respectively formed with the claws 47a protruding toward sides opposite to each other.

In addition, as shown in FIGS. 21(A) and 21(B), similarly to the second embodiment, one coil spring 402 is provided as a spring (biasing member) of an auxiliary mechanism 40 instead of the pair of coil springs 401.

As shown in FIG. 21(A), in an unused state (initial state), the pair of claws 47a of the outer cylinder 4 and the pair of engagement portions 5101 are engaged with each other, and movement of the outer cylinder 4 to the plunger 51 in the distal direction is inhibited.

As shown in FIG. 21(B), in a state where the needle tip side cap 15 and the cap 18 are removed and the outer cylinder 4 is rotated with respect to the cover member 6, the inner cylinder 3, and the operation member 5, each of the claws 47a and each of the engagement portions 5101 are disengaged, and each of the engagement portions 5101 is retreated from each of the plate shaped portions 5102 (main body portions 511) when seen from the axial direction of the plunger 51. Accordingly, it is possible to move the plunger 51 in the distal direction without interfering with each of the claws 47a.

Accordingly the liquid administration device 10, the same effect as that in the aforementioned first embodiment can be obtained.

Moreover, in the liquid administration device 10, in an unused state, each of the claws 47a of the outer cylinder 4 and the each of the engagement portions 5101 of the plunger 51 are engaged and the movement of the outer cylinder 4 to the plunger 51 in the distal direction is inhibited, and therefore, it is possible to prevent the cover member 6, the inner cylinder 3, and the outer cylinder 4 from moving in the distal direction together with the cap 18 while removing the cap 18.

In addition, since each of the claws 47a of the outer cylinder 4 and each of the engagement portions 5101 of the plunger 51 are engaged, it is possible to reliably prevent each of the stepped portions 516 of the plunger 51 from being deviated from positions at which each of the stepped portions 516 is engaged or can be engaged with the slope 491a of each of the spurs 49a of the outer cylinder 4 even when an impact is applied to the liquid administration device 10 by dropping the liquid administration device 10 or the like.

Fifth Embodiment

Figure 24:
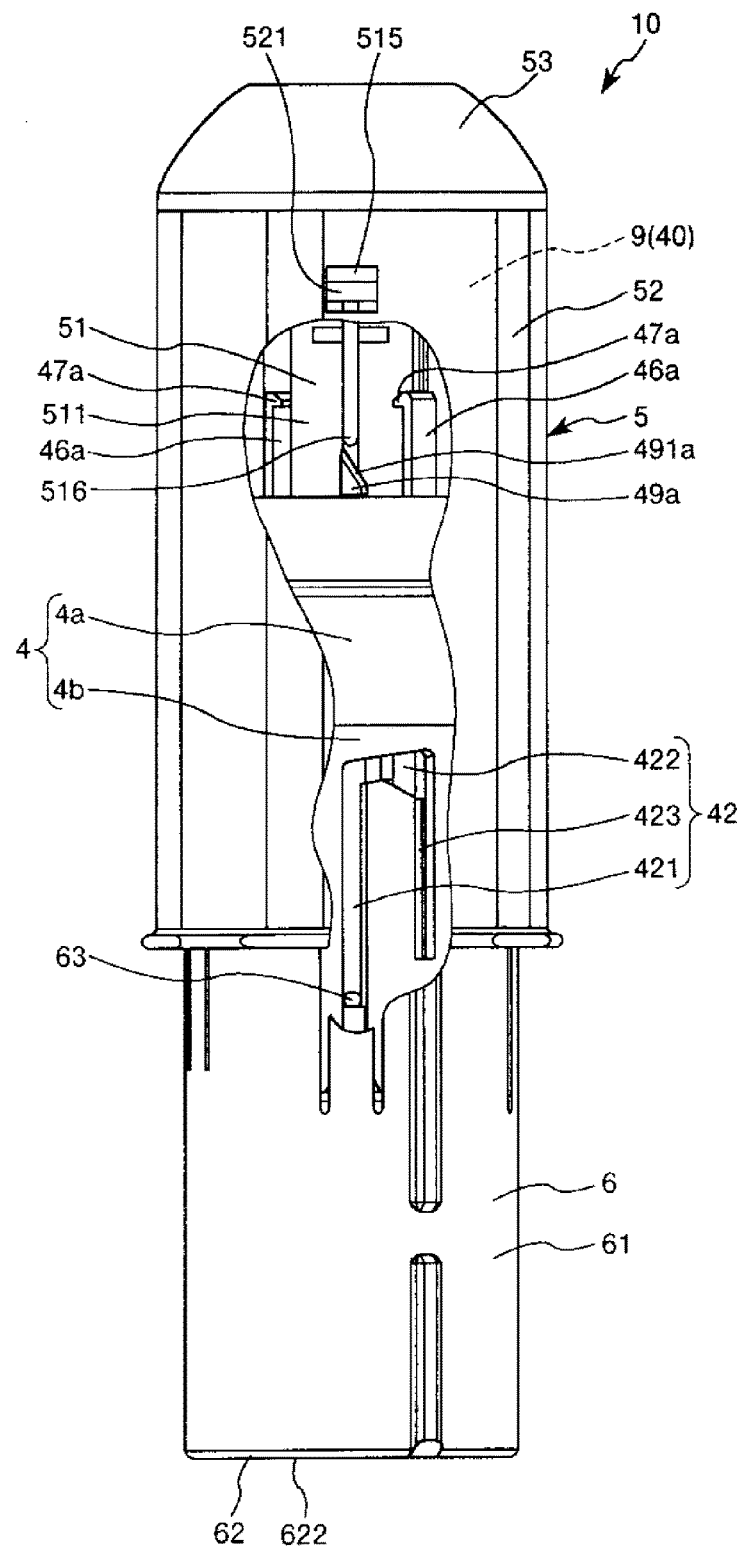
FIG. 24 is a side view showing a fifth embodiment of a liquid administration device of the present invention.
Figure 25:
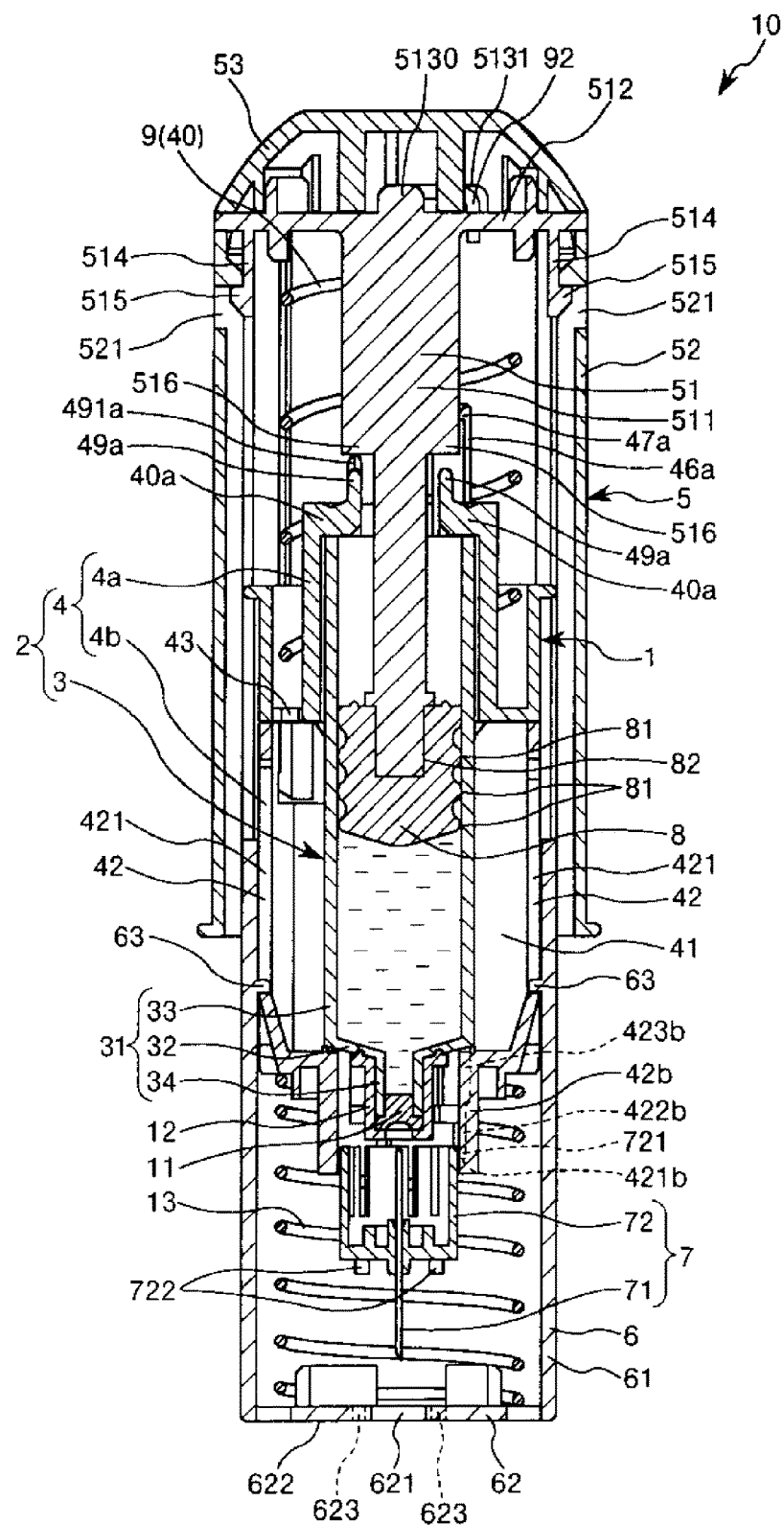
FIG. 25 is a longitudinal sectional view of the liquid administration device shown in FIG. 24.
Figure 26:
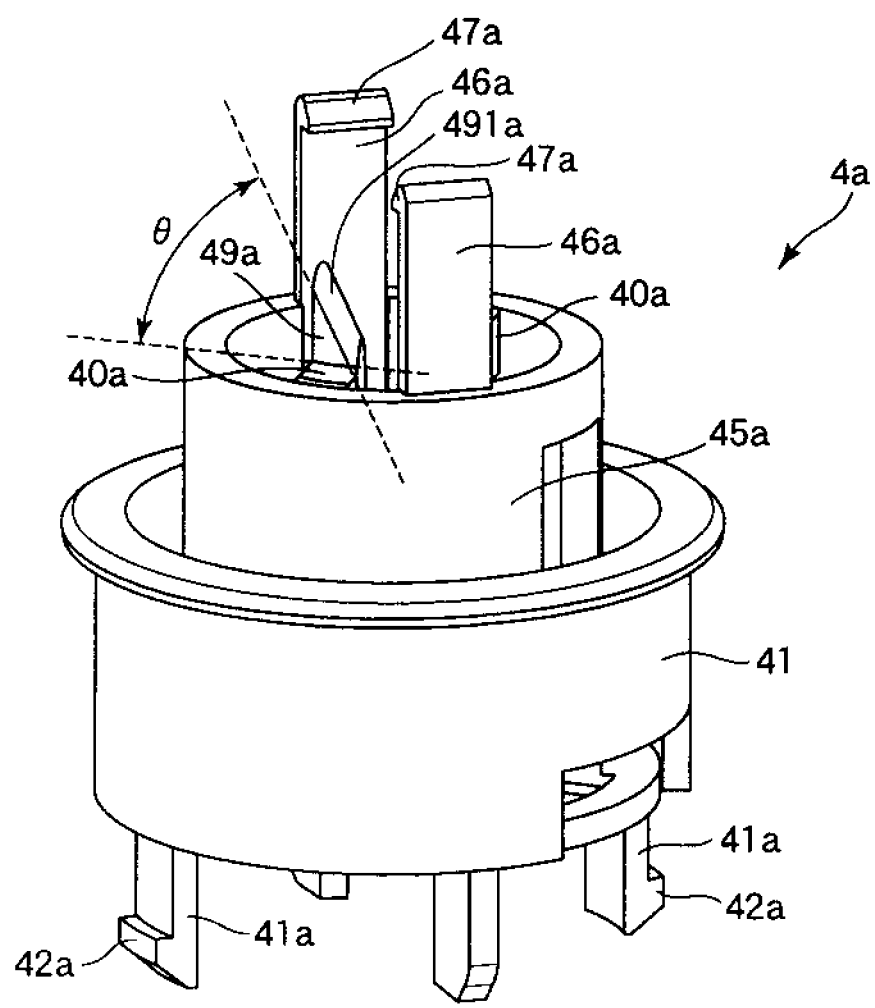
FIG. 26 is a perspective view of a proximal side member of an outer cylinder of a cylindrical body of the liquid administration device shown in FIG. 24.
Figure 27:
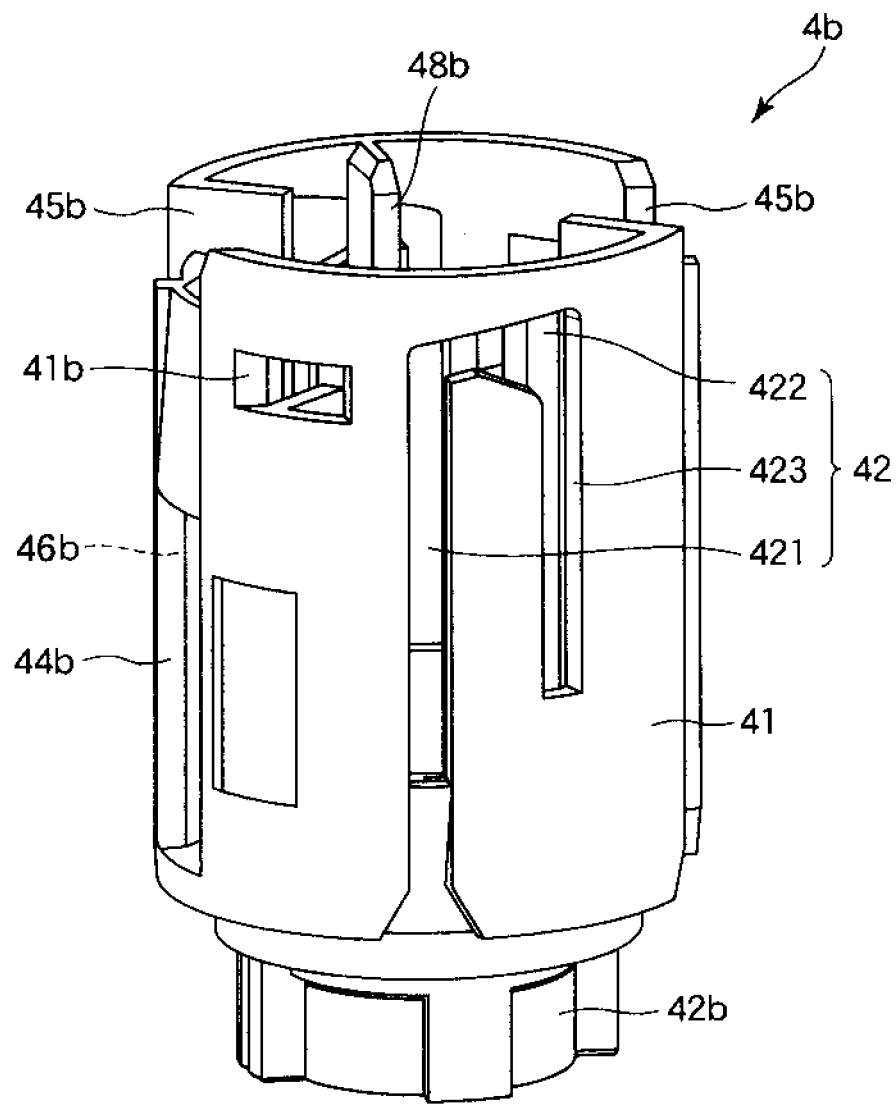
FIG. 27 is a perspective view of a distal side member of the outer cylinder of the cylindrical body of the liquid administration device shown in FIG. 24.
Figure 28:
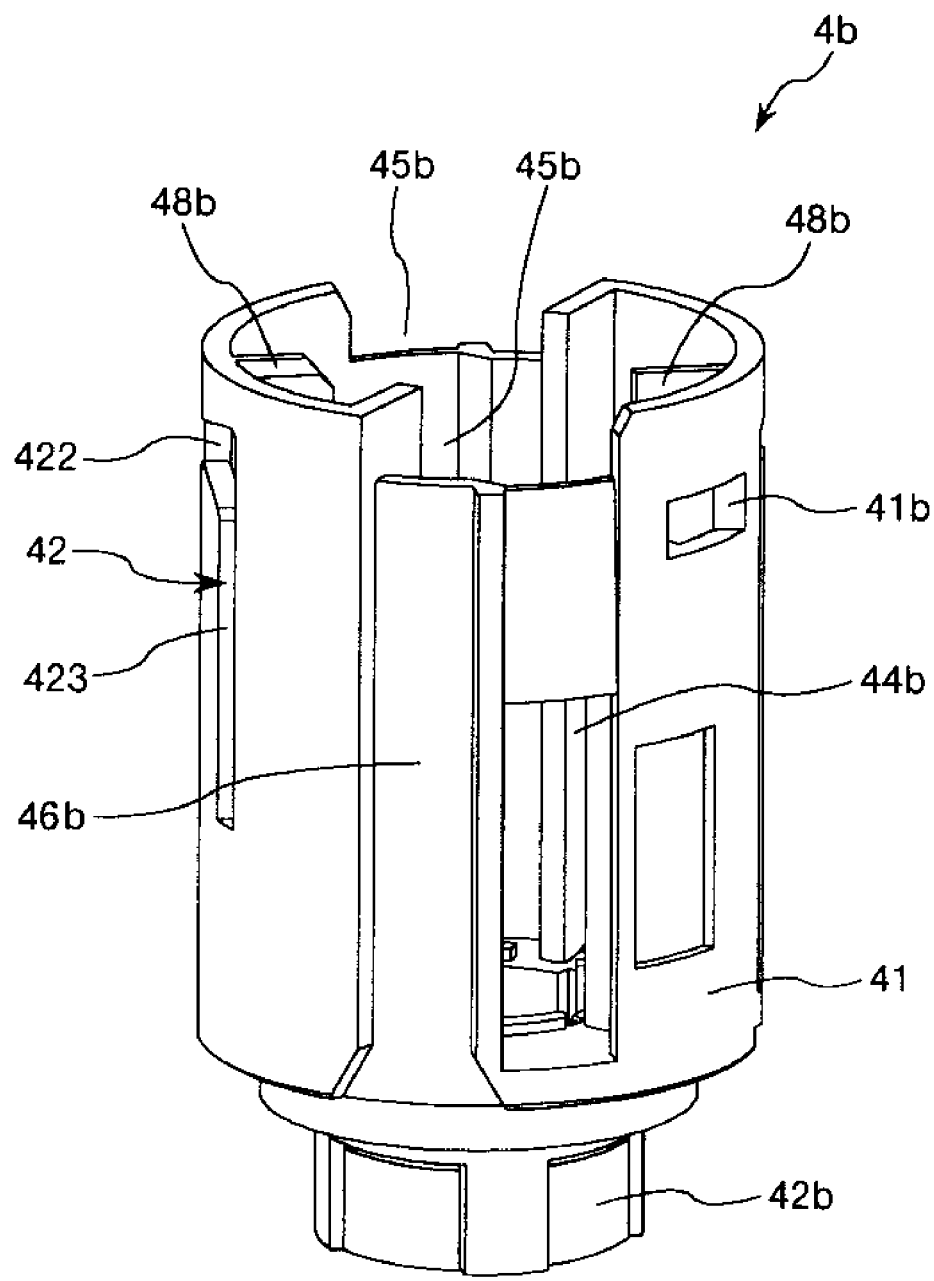
FIG. 28 is a second perspective view of the distal side member of the outer cylinder of the cylindrical body of the liquid administration device shown in FIG. 24.
Figure 29:
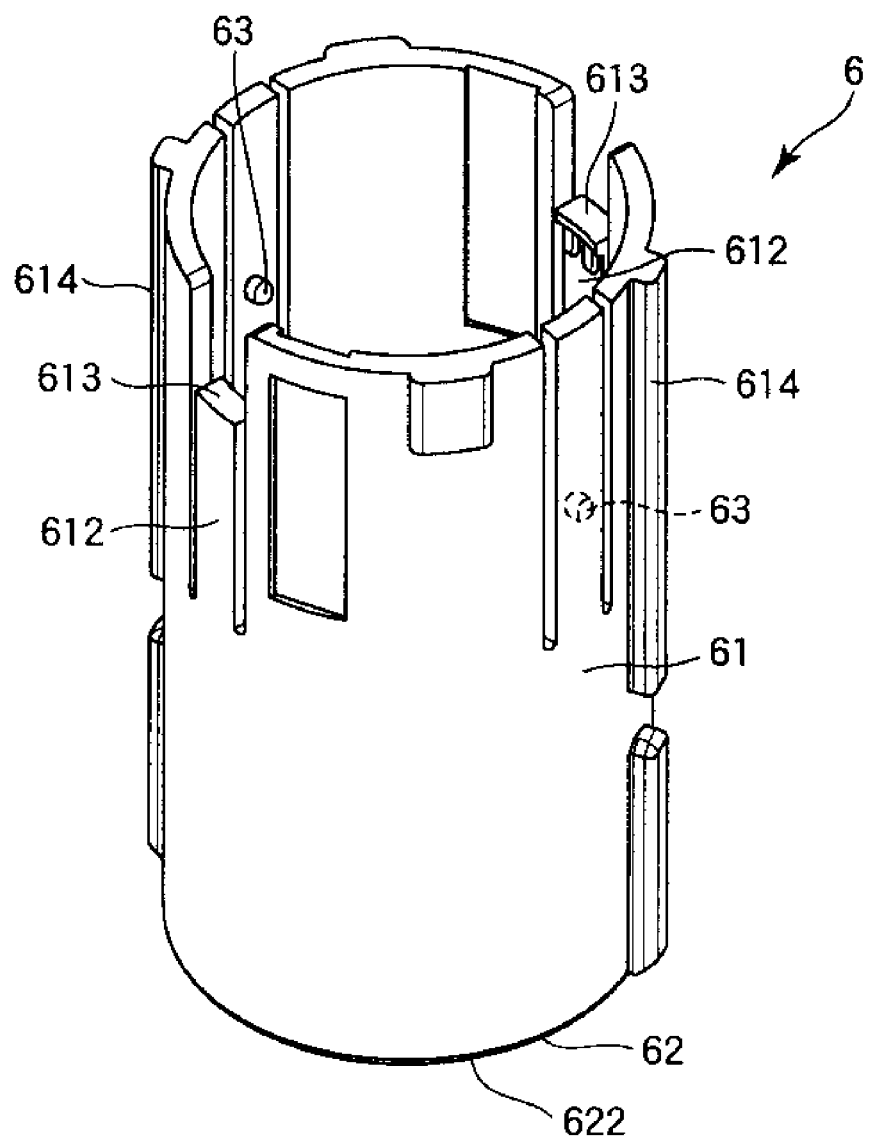
FIG. 29 is a perspective view of a cover member of the liquid administration device shown in FIG. 24.
Figure 30:
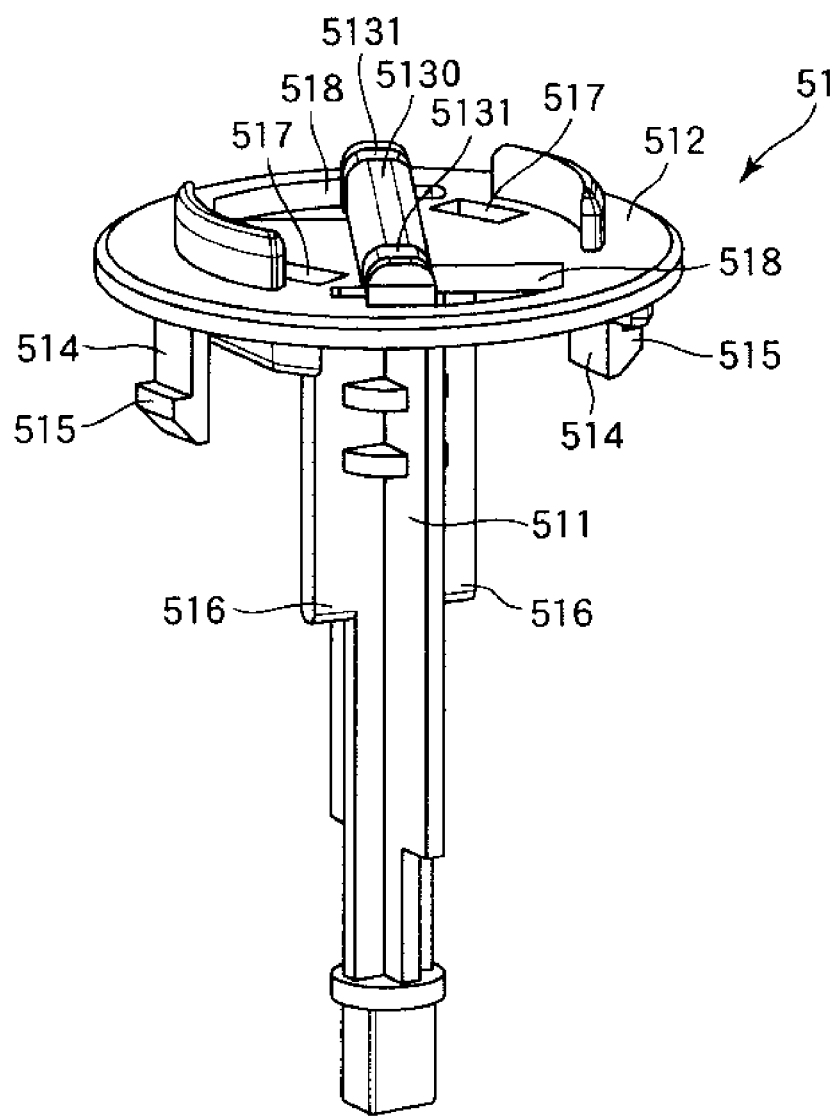
FIG. 30 is a perspective view of a plunger of the liquid administration device shown in FIG. 24.
Figures 31A, 31B, 31C:
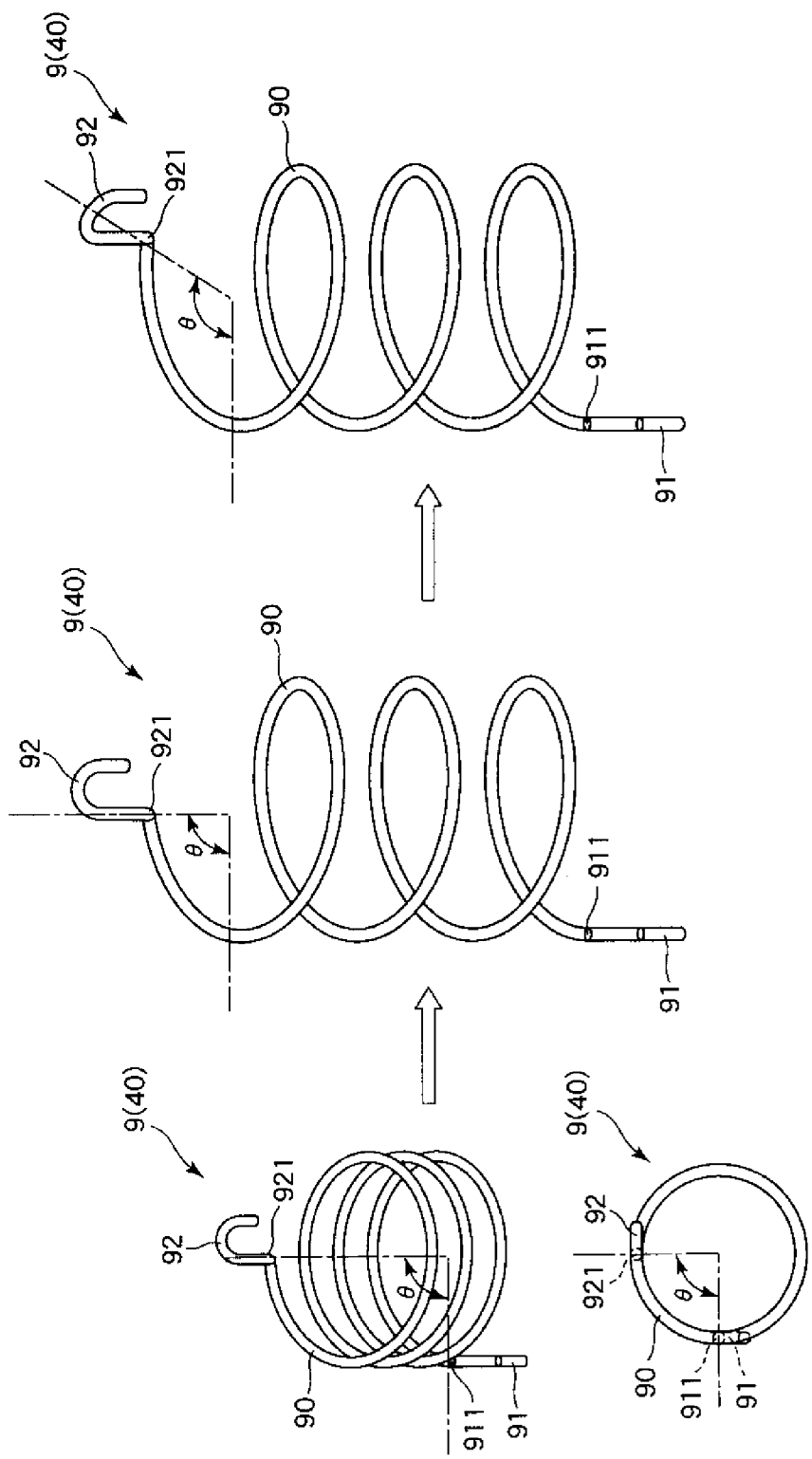
FIG. 31(A) is a perspective view of a coil spring of the liquid administration device shown in FIG. 24 in a natural state.
FIG. 31(B) is a perspective view of the coil spring of the liquid administration device shown in FIG. 24 in a state where the coil spring is extended.
FIG. 31(C) is a perspective view of the coil spring of the liquid administration device shown in FIG. 24 in an initial state.
Figure 32:
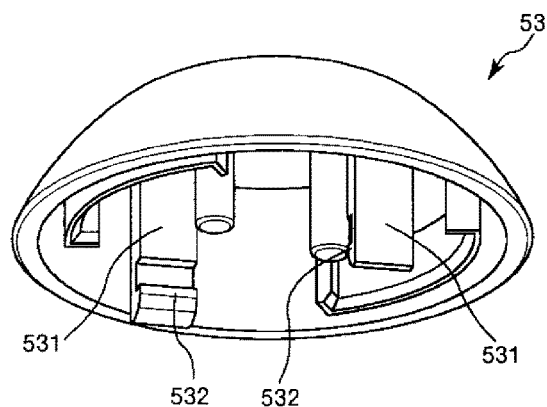
FIG. 32 is a perspective view of a head portion of an operation member of the liquid administration device shown in FIG. 24.

FIG. 24 is a side view showing a fifth embodiment of a liquid administration device of the present invention. FIG. 25 is a longitudinal sectional view of the liquid administration device shown in FIG. 24. FIG. 26 is a perspective view of a proximal side member of an outer cylinder of a cylindrical body of the liquid administration device shown in FIG. 24. FIGS. 27 and 28 are perspective views of a distal side member of the outer cylinder of the cylindrical body of the liquid administration device shown in FIG. 24. FIG. 29 is a perspective view of a cover member of the liquid administration device shown in FIG. 1. FIG. 30 is a perspective view of a plunger of the liquid administration device shown in FIG. 24. FIGS. 31(A) to 31(C) are perspective views of a coil spring of the liquid administration device shown in FIG. 24. FIG. 32 is a perspective view of a head portion of an operation member of the liquid administration device shown in FIG. 24. FIGS. 33, 36, 38, and 40 are respectively a side views showing operation states in use of the liquid administration device shown in FIG. 24 in order. FIGS. 34, 37, 39, 41, and 42 are longitudinal sectional views showing operation states in use of the liquid administration device shown in FIG. 24 in order. FIG. 35 is a cross-sectional view in which a distal portion of the liquid administration device shown in FIG. 34 is taken along another cross section. Note that, hereinafter, the upper side is described as "proximal end (rear end)" or "upper (upward)", the lower side is described as "distal end" or "lower (downward), and the vertical direction is described as "axial direction" or "longitudinal direction" in FIGS. 24 to 42.

Hereinafter, in regard to the fifth embodiment, the difference between the fifth embodiment and the aforementioned first embodiment will be mainly described, and the description of the same matter will not be repeated.

As shown in FIGS. 24 to 28, in the liquid administration device 10 of the fifth embodiment, an outer cylinder 4 is configured to have a proximal side member 4a which is disposed on the proximal side and shown in FIG. 26; and a distal side member 4b which is disposed on the distal side and shown in FIGS. 27 and 28.

Figure 42:
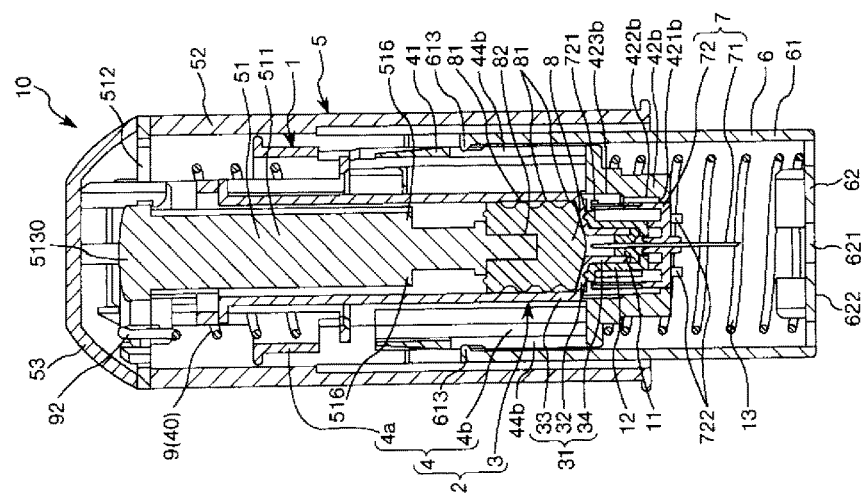
FIG. 42 is a second longitudinal sectional view showing an operation state in use of the liquid administration device shown in FIG. 24 in order, when the cover member is in the fifth position.

Four grooves 422b are formed in an inner peripheral part of a decreased diameter portion 42b of the distal side member 4b, and four stepped portions 421b are formed by the groove 422b (refer to FIGS. 25 and 42). Each of the grooves 422b and each of the stepped portions 421b are arranged at equiangular intervals in parallel along a circumferential direction of the decreased diameter portion 42b. In addition, a space 423b communicating with the grooves 422b is formed on the proximal side of the grooves 422b of the inner peripheral part of the decreased diameter portion 42b (refer to FIGS. 25 and 42). The space 423b makes each of spurs 721 of a support member 72 of a puncture needle 7 to be described later do not interfere with the decreased diameter portion 42b. Note that a decreased diameter portion 45a is formed in the present embodiment, but may not be formed.

In addition, a pair of grooves 46b and a pair of long holes 44b which penetrate a body section 41 are formed on the body section 41 of the distal side member 4b. The grooves 46b are disposed so as to face each other, and similarly, the long holes 44b are also disposed so as to face each other. Note that each of the grooves 46b has an identical shape, and therefore, one groove 46b will be representatively described hereinafter. Similarly, each of the long holes 44b has an identical shape, and therefore, one long hole 44b will be representatively described hereinafter. Note that the groove 46b has a bottom in the present embodiment, but may penetrate the body section 41, and the same effect can be obtained even in this case (not shown). In addition, the long hole 44b penetrates the body section 41 in the present embodiment, but may be sunken without penetrating the body section and the same effect can be obtained even in this case (not shown).

In addition, the grooves 46b and the long holes 44b are arranged in parallel along the circumferential direction of the body section 41. Note that, in the present embodiment, as shown in FIG. 28, the groove 46b is disposed on the left side of the long hole 44b.

In addition, the grooves 46b and the long holes 44b extend along an axis of the body section 41. The groove 46b is formed from a distal end to a proximal end of the distal side member 4b and is opened at the distal end and the proximal end of the distal side member 4b. The end surface of the long hole 44b on the proximal side is positioned further on the distal side than the proximal end of the groove 46b, and is set to be perpendicular to the axis of the body section 41.

In addition, a space 45b is formed in parts of the groove 46b and the long hole 44b on the proximal side in the body section 41.

In addition, the wall thickness of part between the long hole 44b and the space 45b of the body section 41 is gradually decreased from the distal side to the proximal side, and accordingly, a tapered surface is formed on the outer peripheral surface of the body section 41. Accordingly, a spur 613 of a cover member 6 can smoothly move from the space 45b to the long hole 44b.

In addition, a pair of protruding portions 40a which is disposed so as to face each other is formed on the proximal side of the decreased diameter portion 45a of the proximal side member 4a. The protruding portions 40a are protrusively formed toward the inside, that is, toward a central axis from the inner peripheral surface of the decreased diameter portion 45a.

In addition, a spur (second engagement portion) 49a is protrusively formed in an end portion (distal portion) of each of the protruding portions 40a on the central axis side toward the proximal direction.

Each of the spurs 49a has a slope 491a on which each of the stepped portions 516 abuts as a rotary mechanism (rotary portion). Note that the shape of the slope 491a may be a curved surface without being limited to the plane. In addition, the surface may be a flat surface instead of being the slope 491a.

In addition, a pair of elastic arm portions 46a which is disposed so as to face each other is protrusively formed on the proximal side of the decreased diameter portion 45a of the proximal side member 4a in the proximal direction, and a claw 47a which protrudes inward is formed in the distal portion of each of the arm portions 46a.

In addition, movement of the inner cylinder 3 to the outer cylinder 4 in the axial direction is inhibited by the inner cylinder 3 being installed between each of the protruding portions 40a and the decreased diameter portion 42b, of the outer cylinder 4 and being interposed between the proximal side member 4a and the distal side member 4b from upper and lower sides.

In addition, four spurs 722 which protrude toward the distal direction are arranged at equiangular intervals in parallel on the distal surface of the support member 72 of the puncture needle 7 along the circumferential direction thereof (refer to FIGS. 25 and 35).

As shown in FIGS. 25 and 29, the cover member 6 is disposed on the outer peripheral side of the outer cylinder 4 (cylindrical body 2).

Four hole portions 623 which penetrate a distal end wall part 62 of the cover member 6 are formed at equiangular intervals along the circumferential direction of the distal end wall part 62 on the outer peripheral side of the opening portion 621 of the distal end wall part 62 of the cover member (refer to FIGS. 25 and 35). Each of the hole portions 623 is disposed at a position corresponding to each of the spurs 722 of the support member 72 of the puncture needle 7 when seen in a plan view of the cover member 6 so that each of the spurs 722 can be inserted therein. As shown in FIG. 35, in a state where a living body is punctured with the distal side needle tip of the double ended needle 71, each of the spurs 722 is inserted in each of the hole portions 623, and accordingly, it is possible to prevent the puncture needle 7 from rotationally moving in the circumferential direction when administering a liquid.

In an unused state (initial state), each of the spurs 613 of the cover member 6 is inserted in each of the grooves 46b of the outer cylinder 4. When the cover member 6 moves in the axial direction of the outer cylinder 4, and when the outer cylinder 4 is rotated with respect to the cover member 6 at a predetermined angle by a cam groove 42 of the outer cylinder 4 and the spur 63 of the cover member 6, each of the spurs 613 of the cover member 6 moves to positions on the proximal side of each of the long holes 44b in each of the spaces 45b of the outer cylinder 4.

As shown in FIGS. 24 and 25, the operation member 5 has a head portion 53, an outermost cylinder (grip portion) 52, and a plunger 51 which is interlocked with the gasket 8 on the proximal side and presses the gasket 8 toward the distal direction. The head portion 53, the plunger 51, and the outermost cylinder 52 are interlocked with each other. The operation member 5 is a member which performs a pressing operation (discharging operation) to discharge a liquid in the inner cylinder 3 from the double ended needle 71 by moving the gasket 8 in the distal direction using the plunger 51 moving in the distal direction.

As shown in FIGS. 25 and 30, the plunger 51 has a bar-shaped main body portion 511 whose cross section is, for example, a cross-shaped or a circular-shape, and the gasket 8 is fixed to the distal end of the main body portion 511. A disk-shaped flange 512 is formed at the proximal end of the main body portion 511.

The distal portion of the main body portion 511 has a shape corresponding to the shape of a recess portion 82 of the gasket 8, and the plunger 51 (operation member 5) and the gasket 8 are interlocked with each other by the distal portion of the main body portion being inserted in the recess portion 82 of the gasket 8.

A pair of hole portions 517 which is disposed so as to face each other across a center of the plunger 51, and a pair of hole portions 518 which is disposed so as to face each other across the center of the plunger, are formed on the flange 512 of the plunger 51. In addition, the hole portions 517 and the hole portions 518 are alternately disposed.

In addition, a rib 5130 which extends in the radial direction of the flange 512 is formed in the central portion of the flange 512 on the proximal side. Grooves 5131 are respectively formed in both end portions of the rib.

The head portion 53 is installed on the proximal side of the outermost cylinder 52 and on the proximal side of the flange 512 of the plunger 51. As shown in FIGS. 25 and 32, the head portion 53 forms a mortar shape. The central portion of the proximal surface, that is, the outer surface of the head portion 53 is flat and the periphery thereof is curved such that the proximal side is projected. It is possible to easily grip the operation member 5 with one hand using the head portion 53 having the curved surface. In addition, when performing a pressing operation with both hands, it is possible to easily perform the pressing operation using the flat surface formed on the central portion of the head portion 53.

In addition, a pair of elastic arm portions 531 which is disposed in the distal direction so as to face each other is protrusively formed on the distal surface of the head portion 53, that is, in the outer peripheral portion of the inner surface, and a claw 532 which protrudes inward is formed in the distal portion of each of the arm portions 531.

The claws 532 of each of the arm portions 531 of the head portion 53 are disposed in the hole portions 518, and the claws 532 and the hole portions 518 are engaged with each other. As a result, the head portion 53 and the plunger 51 are interlocked with each other.

An auxiliary mechanism 40 has a function of generating auxiliary force (pressing force) for pressing the gasket 8 through the plunger 51 of the operation member 5. As shown in FIGS. 25 and 31(A) to 31(C), in the present embodiment, the auxiliary mechanism 40 is constituted by a single coil spring 9. In addition, the coil spring 9 is a tension spring used in a state of being extended. The coil spring 9 has a coil spring main body 90; a hook 91 as a first attachment portion which is provided in the distal portion of the coil spring main body 90 and attached to an inner structure 1; and a hook 92 as a second attachment portion which is provided in the proximal portion of the coil spring main body 90 and attached to the operation member 5.

The shapes of the hooks 91 and 92 are not particularly limited, but form a U shape in the present embodiment. Note that examples of other shapes include a V shape or a C shape.

Figure 37:
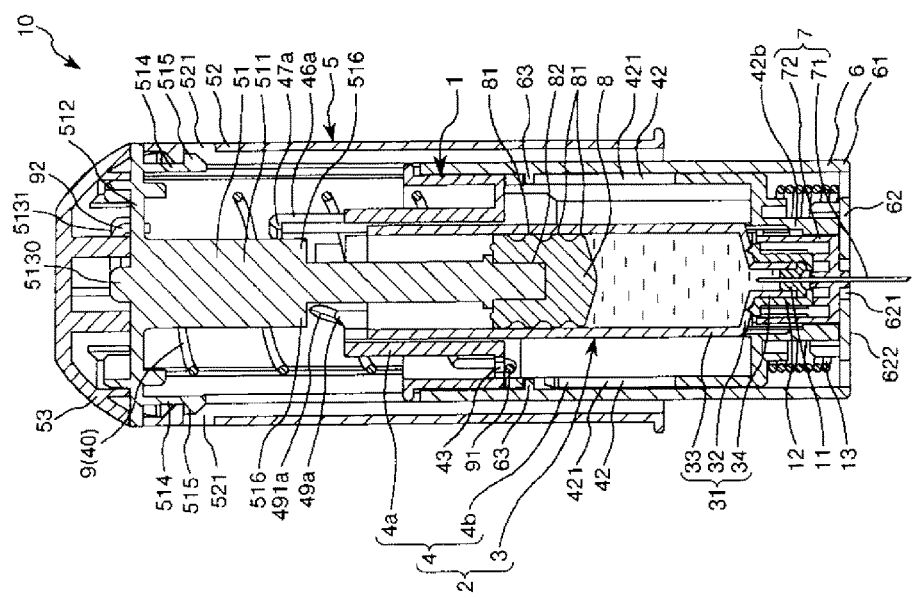
FIG. 37 is a longitudinal sectional view showing an operation state in use of the liquid administration device shown in FIG. 24 in order, when the cover member is in the third position.

In addition, the plunger 51 is disposed inside the coil spring 9 when seen from the axial direction of the coil spring 9, and the coil spring 9 is wound along the outer periphery of the plunger 51, that is, concentrically disposed with the plunger 51 and the cylindrical body 2 on the outer peripheral side of the plunger 51. As shown in FIGS. 25, 31(B), and 37, the hook 91 is placed on a support portion 43 of the outer cylinder 4 which forms a bar shape and the hook 92 is placed in the groove 5131 of the rib 5130 of the plunger 51 in a state where the coil spring 9 is extended.

Accordingly, the coil spring 9 biases the inner structure 1 and the operation member 5 in directions approaching to each other. That is, the coil spring 9 generates an auxiliary force which presses the gasket 8 in the distal direction through the plunger 51 of the operation member 5. Accordingly, during the pressing operation, it is possible to easily move the operation member 5 in the distal direction.

In addition, the positions of the hooks 91 and 92 of the coil spring 9 are not particularly limited, and can be appropriately set depending on the conditions. In the present embodiment, the hooks 91 and 92 are respectively disposed on a circuit of a winding wire of the coil spring 9 when seen from the axial direction of the coil spring 9. In addition, an end portion 921 of the hook 92 on the coil spring main body 90 side is preferably positioned at a position deviated by a central angle of −135° to 135°, and more preferably at a position deviated by a central angle of −110° to −45°, or 45° to 110°, in a winding direction of the coil spring 9 with respect to an end portion 911 of the hook 91 on the coil spring main body 90 side in a natural state (refer to FIG. 31(A)) where no external force is applied to the coil spring 9 when seen from the axial direction of the coil spring 9. Note that the angle of the central angle is regarded as θ. In addition, the angle θ is regarded as "0°" in a case where the end portion 921 of the hook 92 and the end portion 911 of the hook 91 are coincide with each other when seen from the axial direction of the coil spring 9, and the angle in a clockwise direction in FIGS. 31(A) to 31(C) is regarded as "+" and the angle in a counterclockwise direction in FIGS. 31(A) to 31(C) is regarded as "−". In the configuration shown in the drawing, the angle θ is 90°, that is, the end portion 921 is positioned at a position deviated by a central angle of 90° with respect to the end portion 911 in the winding direction of the coil spring 9.

Accordingly, when the coil spring 9 is extended, it is possible to prevent or suppress the ring of the winding wire of the coil spring 9 from being deviated in a radial direction, and accordingly, it is possible to prevent the coil spring 9 from being brought into contact with the outer peripheral surface of the plunger 51. Accordingly, it is possible to smoothly and reliably administer a liquid.

Note that, in the winding direction of the coil spring 9 when describing the positions of the hooks 91 and 92, a counterclockwise direction in FIGS. 31(A) to 31(C) is the winding direction of the coil spring 9 when describing the position of the hook 91 with respect to the hook 92 of the coil spring 9, and a clockwise direction in FIGS. 31(A) to 31(C) is the winding direction of the coil spring 9 when describing the position of the hook 92 with respect to the hook 91 of the coil spring 9.

Here, during the pressing operation of the operation member 5 for administering a liquid, the biasing force (pressing force) of the coil spring 13 as well as the biasing force of the coil spring 9 generates an auxiliary force which presses the gasket 8 in the distal direction through the plunger 51 of the operation member 5. That is, the plunger 51 moves in the distal direction using the pressing force which a user presses the operation member 5 (plunger 51) in the distal direction, the biasing force of the coil spring 9, and the biasing force of the coil spring 13.

Specifically, when the biasing force (pressing force) of the coil spring 9 is set to F1, the biasing force of the coil spring 13 is set to F2, and the discharge resistance force which contains a dynamic frictional resistance force of the gasket 8 while sliding to the inner cylinder 3 (cylindrical body 2) is set to F0, F0, F1, and F2 are set so as to satisfy the following equation (1).

$$F1+F2 \geq F0 \qquad (1)$$

Accordingly, when administering a liquid, it is possible to prevent the liquid from being administered by the plunger 51 automatically moving in the distal direction without exerting force for sliding the gasket 8 which is exerted by a user. That is, it is possible to administration a liquid as intended by a user. For example, it is possible to administer a liquid at a user's pace and to instantly suspend the administration of a liquid when it is necessary to suspend the administration of a liquid.

In addition, F1 is preferably 1 N to 40 N and more preferably 1 N to 10 N. When F1 is smaller than the lower limit value, there is a concern that the auxiliary force may become more insufficient depending on other conditions. In addition, when F1 is greater than the upper limit, there is a concern that F2 may be decreased depending on other conditions and the distal side needle tip of the double ended needle 71 may be exposed from the distal end of the cover member 6.

In addition, F2 is preferably 1 N to 5 N and more preferably 1 N to 3 N. When F2 is smaller than the lower limit value, there is a concern that the distal side needle tip of the double ended needle 71 may be exposed from the distal end of the cover member 6 depending on other conditions. In addition, when F2 is greater than the upper limit, it is difficult to move the cover member 6 in the proximal direction against the biasing force of the coil spring 13 depending on other conditions.

In addition, as shown in FIG. 31(C), in an unused state (initial state), the coil spring 9 is attached in a state of being twisted in the circumferential direction thereof from the natural state, and one of the outer cylinder 4 and the operation member 5 is biased to the other in a rotational direction of the cylindrical body 2 around the central axis. Accordingly, it is possible to easily administer a liquid when administering a liquid by obtaining force which rotates the outer cylinder 4 with respect to the operation member 5, the cover member 6, and the inner cylinder 3. It is possible to attach the coil spring 9 to the inner structure and the operation member in an unused state without twisting the coil spring.

The torsional direction of the coil spring 9 may be either a winding direction of the coil spring 9 or an opposite direction thereto, and in the present embodiment, the winding direction of the coil spring 9 is employed. It is possible to twist the coil spring 9 without disarranging the shape of the winding wire of the coil spring 9 by setting the torsional direction of the coil spring 9 to be the same as the winding direction of the coil spring 9. When the torsional direction of the coil spring 9 is a direction opposite to the winding direction of the coil spring 9, the diameter of the coil spring 9 during operation is smaller than that in the initial state, and therefore, it is possible to restrict movement of the plunger 51.

In addition, the torsional amount of the coil spring 9 is not particularly limited, and can be appropriately set depending on the conditions. The torsional amount of the coil spring is preferably set equal to the rotary angle when the outer cylinder 4 is relatively rotated with respect to the inner cylinder 3, at an absolute value of the difference between an angle θ before the coil spring 9 is twisted and an angle θ after the coil spring is twisted, that is, an absolute value of the central angle of the coil spring 9. Specifically, the torsional amount of the coil spring 9 is preferably 10° to 90° and more preferably 20° to 40° at the absolute value of the central angle of the coil spring 9. When the torsional amount of the coil spring 9 is smaller than the lower limit value, in some cases, the biasing force of the coil spring 9 disappears before the outer cylinder 4 is completely rotated relatively to the inner cylinder 3 depending on other conditions. In addition, when the torsional amount of the coil spring 9 is greater than the upper limit value, in some cases, the biasing force of the coil spring 9 is applied even after the outer cylinder 4 is completely rotated relatively to the inner cylinder 3 depending on other conditions.

In addition, the dimensions or the characteristics, such as the number of turns of the coil spring 9, the pitch of the coil spring, the diameter (outer diameter) of the coil spring, the length of the coil spring, and the spring constant of the coil spring, are not particularly limited as long as they satisfy the following equation (2), and can be appropriately set depending on the conditions. For example, the number of turns of the coil spring 9 is preferably 2 times to 100 times and more preferably 3 times to 10 times. When the number of turns of the coil spring 9 is smaller than the lower limit value, in some cases, it is impossible to obtain sufficient biasing force depending on other conditions. In addition, when the number of turns of the coil spring 9 is greater than the upper limit, the ring of the winding wire of the coil spring 9 is easily deviated in the radial direction depending on other conditions.

In addition, the pitch of the coil spring 9 is preferably less than or equal to 10 mm and more preferably 0.1 mm to 2 mm. When the pitch of the coil spring 9 is smaller than the lower limit value, in some cases, it is impossible to obtain sufficient biasing force depending on other conditions. In addition, when the pitch of the coil spring 9 is greater than the upper limit value, the ring of the winding wire of the coil spring 9 is easily deviated in the radial direction depending on other conditions.

In addition, the diameter (outer diameter) of the coil spring 9 is preferably 5 mm to 50 mm and more preferably 10 mm to 30 mm. When the diameter of the coil spring 9 is smaller than the lower limit value, in some cases, it is impossible to obtain sufficient biasing force depending on other conditions. In addition, when the diameter of the coil spring 9 is greater than the upper limit value, the deviation amount of the ring of the winding wire of the coil spring 9 in the radial direction becomes greater depending on other conditions.

In addition, the length of the coil spring 9 in a natural state where no external force is applied thereto is preferably 3 mm to 150 mm and more preferably 5 mm to 30 mm including the hooks 91 and 92.

In addition, the spring constant of the coil spring 9 is preferably 0.01 N/mm to 4 N/mm and more preferably 0.03 N/mm to 1 N/mm. When the spring constant of the coil spring 9 is smaller than the lower limit value, in some cases, it is impossible to obtain sufficient biasing force depending on other conditions. In addition, when the spring constant of the coil spring 9 is greater than the upper limit value, in some cases, excessive biasing force is exerted depending on other conditions.

Note that the constituent materials of the coil spring 9 are not particularly limited, and for example, it is possible to use the same materials as those of the coil spring 13.

Next, the usage of the liquid administration device 10 and the operation state when in use will be described with reference to FIGS. 24, 25, and 33 to 42.

As shown in FIGS. 24 and 25, the liquid administration device 10 in an unused state (initial state) is prepared. In the liquid administration device 10 in the unused state, the cover member 6 is at the first position and covers the distal side needle tip of the double ended needle 71. Note that, in the unused state, the distal side needle tip of the double ended needle 71 is maintained in a state of being covered with the cover member 6 due to the biasing force of the coil spring 13. Accordingly, erroneous puncturing due to the distal side needle tip of the double ended needle 71 can be reliably prevented.

In addition, in the puncture needle 7, the proximal side needle tip of the double ended needle 71 is separated from the sealing member 11 of the inner cylinder 3 of the cylindrical body 2, and does not pierce the sealing member 11 yet. Accordingly, it is possible to maintain the liquid in an aseptic state until administration of the drug solution starts.

In addition, each of the spurs 63 of the cover member 6 is positioned at a position shown in FIG. 24 with respect to the outer cylinder 4.

In addition, each of the spurs 613 of the cover member 6 is positioned on the proximal side of the groove 46b of the distal portion of the outer cylinder 4.

In addition, each of the stepped portions 516 of the plunger 51 is at a position at which each of the stepped portions abuts or can abut (may be separated before use) on the slope 491a of each of the spurs 49a of the outer cylinder 4, that is, at a position at which each of the stepped portions is engaged or can be engaged with each of the spurs 49a. As a result, the movement of the operation member 5 to the inner structure 1 (cylindrical body 2) in the distal direction is inhibited.

In addition, the spur 63 is disposed in the linear groove 421, and accordingly, the outer cylinder 4 is inhibited from being rotated with respect to the cover member 6. As a result, the outer cylinder 4 is inhibited from being rotated with respect to the operation member 5.

Figure 33:
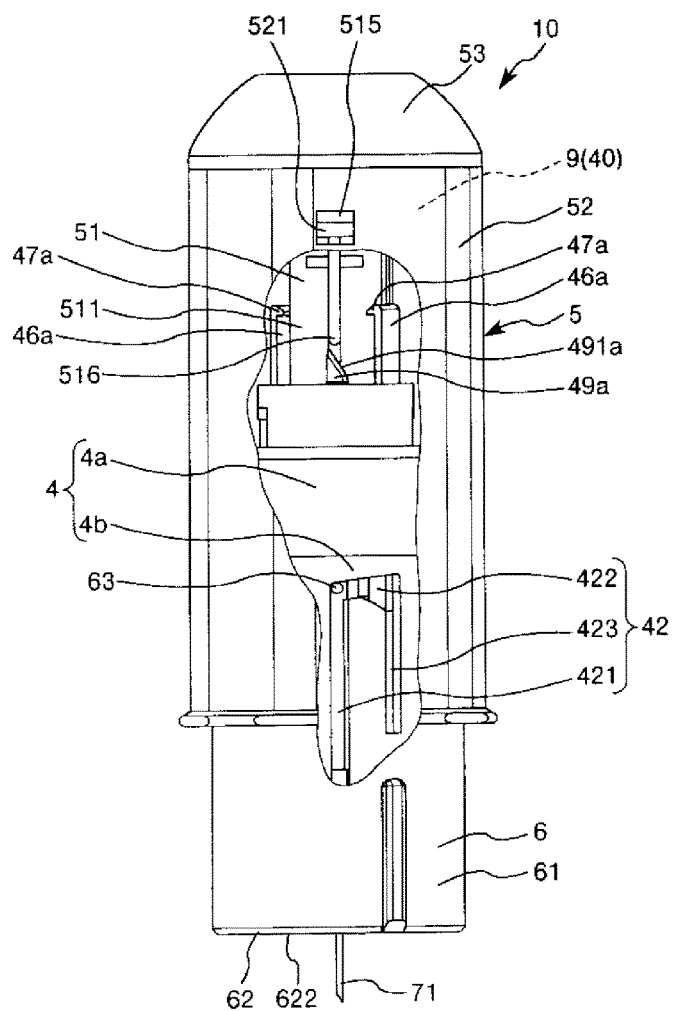
FIG. 33 is a side view showing an operation state in use of the liquid administration device shown in FIG. 24 in order, when the cover member is in a second position.
Figure 34:
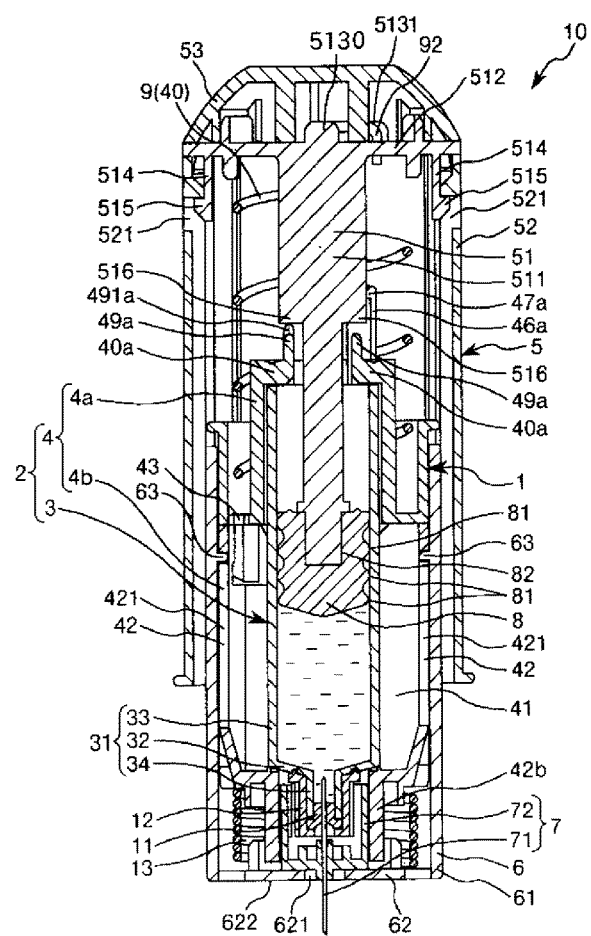
FIG. 34 is a longitudinal sectional view showing an operation state in use of the liquid administration device shown in FIG. 24 in order, when the cover member is in the second position.
Figure 35:
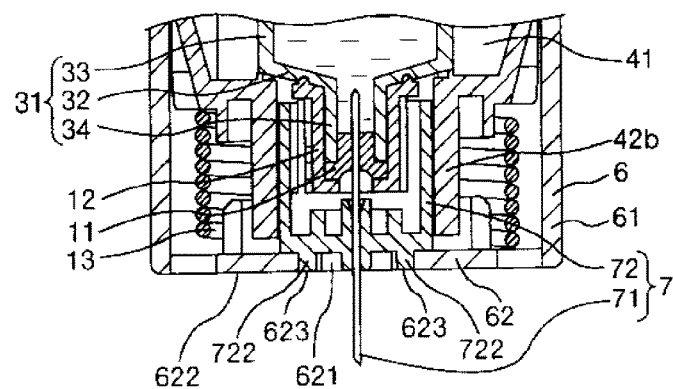
FIG. 35 is a cross-sectional view in which a distal portion of the liquid administration device shown in FIG. 34 is taken along another cross section.

Next, as shown in FIGS. 33 and 34, the operation member 5 of the liquid administration device 10 in the unused state is gripped, the distal end wall part 62 of the cover member 6 is abutted on a living body, and the operation member 5 is pressed toward the distal direction. Accordingly, the cover member 6 moves to the operation member 5 and the inner structure 1 in the proximal direction, that is, from the first position to the second position against the biasing force of the coil spring 13. In addition, in the moving process, the distal end wall part 62 of the cover member 6 moves the support member 72 of the puncture needle 7 to the proximal portion side.

At this time, the distal side needle tip of the double ended needle 71 protrudes from the opening portion 621 of the distal end wall part 62 of the cover member 6, and the living body is punctured with the distal side needle tip. In addition, the distal end wall part 62 presses the support member 72 of the puncture needle 7 toward the proximal direction. Accordingly, it is possible to pierce the sealing member 11 of the inner cylinder 3 with the proximal side needle tip of the double ended needle 71, and thus, the double ended needle 71 puncturing the living body communicates with the inner cylinder 3.

At this time, the spur 63 of the cover member 6 moves relative to the outer cylinder 4 in the proximal direction along the linear groove 421. When the cover member 6 is at the second position, the spur 63 of the cover member 6 is positioned at a position shown in FIG. 33 with respect to the outer cylinder 4.

In addition, each of the spurs 613 of the cover member 6 at this time is in a state where each of the spurs moves in the proximal direction along each of the grooves 46b of the outer cylinder 4 and is positioned in each of the spaces 45b (refer to FIG. 28) of each of the grooves 46b on the proximal side.

In addition, the spurs 722 of the puncture needle 7 are disposed in the hole portions 623 of the cover member 6, and as a result, the puncture needle 7 is prevented from being rotated in the circumferential direction.

In addition, the spur 63 is positioned in the proximal portion of the linear groove 421, and accordingly, the outer cylinder 4 can be rotated with respect to the cover member 6. As a result, the outer cylinder 4 can be rotated with respect to the operation member 5.

Figure 36:
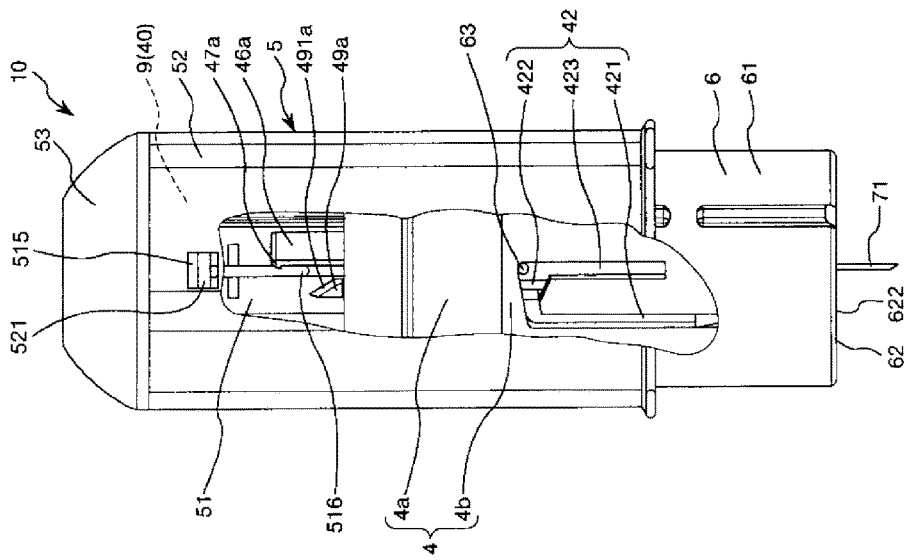
FIG. 36 is a side view showing an operation state in use of the liquid administration device shown in FIG. 24 in order, when the cover member is in a third position.

Next, when the operation member 5 is continuously pressed in the distal direction in the state shown in FIGS. 33 and 34, the cover member 6 reaches the third position as shown in FIGS. 36 and 37. This state is a state in which the rotation of the outer cylinder 4 with respect to the cover member 6 and the inner cylinder 3 at a predetermined angle due to the cam groove 42 of the outer cylinder 4 and the spur 63 of the cover member 6 has been finished.

At this time, the stepped portion 516 of the plunger 51 moves along the slope 491a of the spur 49a, and at this time, the outer cylinder 4 obtains propulsive force in the rotational direction. Furthermore, the outer cylinder 4 obtains propulsive force in the rotational direction using the biasing force of the coil spring 9 in the rotational direction. Accordingly, it is possible to easily rotate the outer cylinder 4.

Accordingly, each of the stepped portions 516 of the plunger 51 moves to a position of being deviated from each of the spurs 49a of the outer cylinder 4, and enters a state where each of the stepped portions 516 and each of the spurs 49a are disengaged. Accordingly, the operation member 5 can move to the cylindrical body 2 in the distal direction. After that, the state where each of the stepped portions 516 and each of the spurs 49a are disengaged is maintained, and therefore, the description thereafter will not be repeated.

Note that the operation of puncturing a living body with the double ended needle 71, the rotational operation of the outer cylinder 4, and the pressing operation of the operation member 5 to be described later can be smoothly performed as a continuous operation.

In addition, the spur 63 of the cover member 6 relatively moves to the outer cylinder 4 along the inclined groove 422 in an oblique upward direction. Then, when the cover member 6 is in the third position, the spur 63 of the cover member 6 is positioned at the position shown in FIG. 36 with respect to the outer cylinder 4.

In addition, at this time, each of the spurs 613 of the cover member 6 is rotated and enters a state where the each of the spurs moved to the position on the proximal side of the each of the long holes 44b in each of the spaces 45b.

Figure 38:
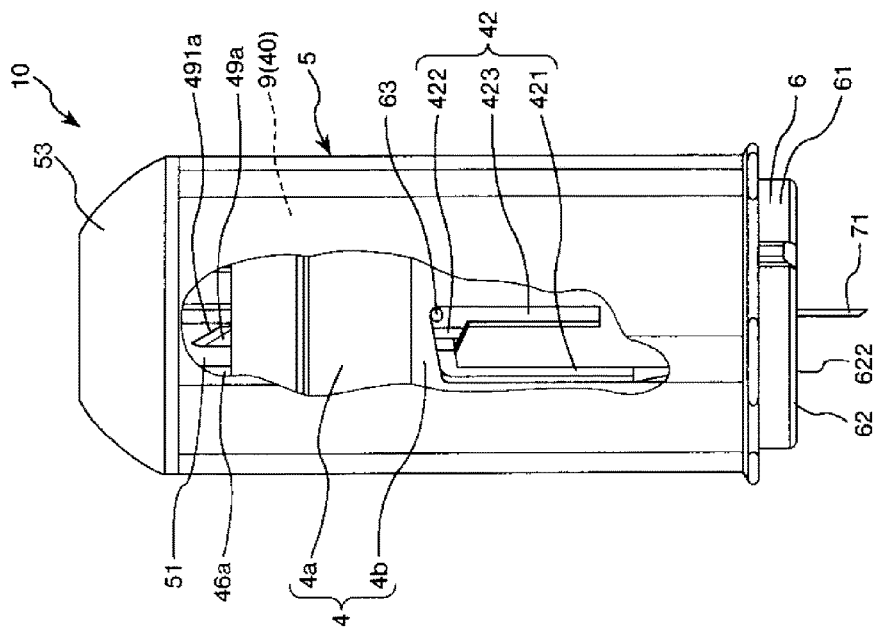
FIG. 38 is a side view showing an operation state in use of the liquid administration device shown in FIG. 24 in order, when the cover member is in a fourth position.
Figure 39:
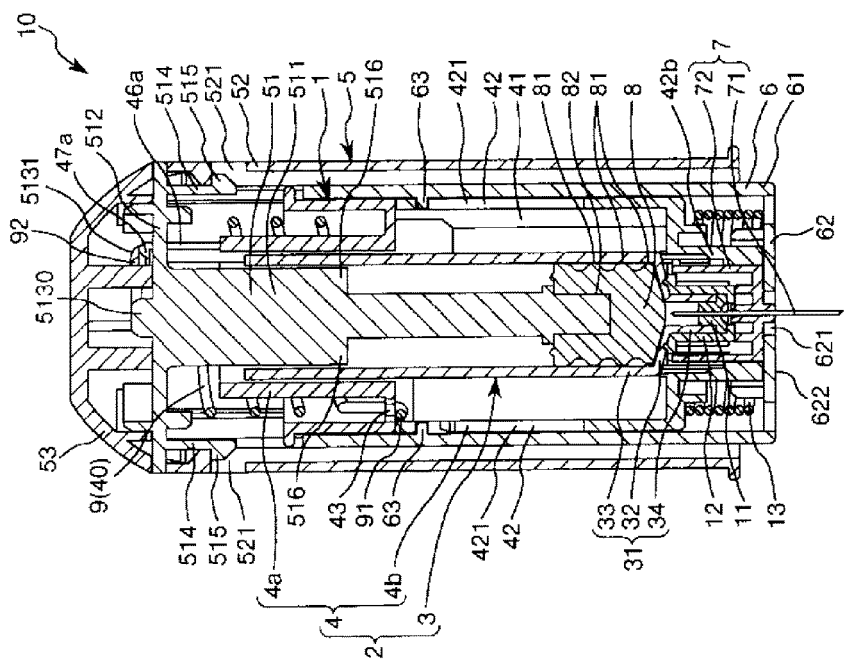
FIG. 39 is a longitudinal sectional view showing an operation state in use of the liquid administration device shown in FIG. 24 in order, when the cover member is in the fourth position.

As shown in FIGS. 36 and 37, the operation member 5 moves in the distal direction using the pressing force of a user, and the biasing force of the coil spring 9, that is, the auxiliary force (pressing force) thereof in the state where the cover member 6 is positioned at the third position, and accordingly, the gasket 8 can move toward the distal direction. That is, the aforementioned pressing operation is performed, and therefore, it is possible to perform administration of a liquid. As shown in FIGS. 38 and 39, the gasket 8 abuts on the bottom part 32 of the inner cylinder 3, the administration of a liquid is completed, and the cover member 6 is positioned at the fourth position.

At this time, the spur 63 of the cover member 6 is maintained at the position shown in FIG. 38 with respect to the outer cylinder 4.

In addition, each of the spurs 613 of the cover member 6 is also maintained at the position on the proximal side of each of the long holes 44b in each of the spaces 45b.

In addition, the claws 47a of the arm portions 46a of the outer cylinder 4 are disposed in the hole portions 517 of the plunger 51 to be engaged with the hole portions 517. At this time, the end of each of the arm portions 46a is bent and returns to its original shape using elastic force at the moment that each of the claws 47a protrudes from the hole portions 517 in the proximal direction, thereby generating a sound (audible sound) and a vibration (click feeling) from each of the arm portions 46a. Accordingly, a user can recognize that the administration of a liquid is completed.

In addition, after use, the outer cylinder 4 and the operation member 5 are fixed to each other through engagement of each of the claws 47a and each of the hole portions 517. Accordingly, it is possible to restrict the movement of the operation member 5 after use, and the user can recognize that the device is in a state where the administration has been completed.

Figure 40:
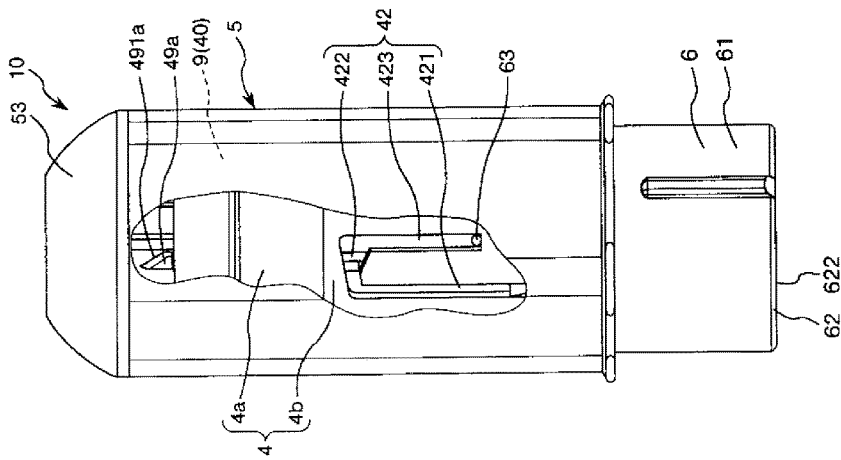
FIG. 40 is a side view showing an operation state in use of the liquid administration device shown in FIG. 24 in order, when the cover member is in a fifth position.
Figure 41:
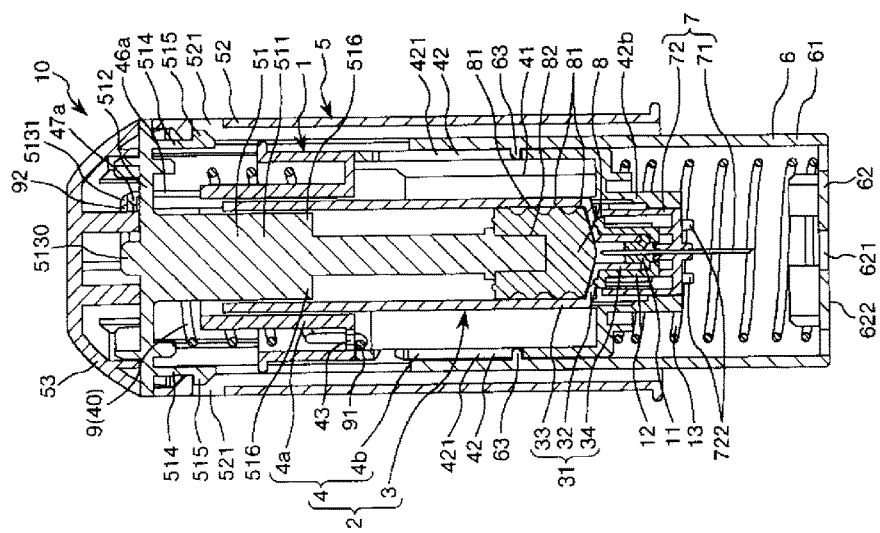
FIG. 41 is a longitudinal sectional view showing an operation state in use of the liquid administration device shown in FIG. 24 in order, when the cover member is in the fifth position.

Next, as shown in FIGS. 40 to 42, the pressing of operation member 5 toward the distal direction is stopped, the distal end wall part 62 of the cover member 6 is separated from a living body, and the double ended needle 71 is removed from the living body.

Accordingly, the cover member 6 moves in the distal direction, that is, to the fifth position using the biasing force of the coil spring 13, and the distal side needle tip of the double ended needle 71 is covered with the cover member.

In addition, the cover member 6 is inhibited from moving to the outer cylinder 4 in the proximal direction by each of the spurs 613 of the cover member 6 being engaged with the proximal portion of the long hole 44b. As a result, the state where the distal side needle tip of the double ended needle 71 is covered with the cover member 6 is maintained. Accordingly, the cover member 6 cannot move in the proximal direction, and therefore, functions as a safety mechanism which prevents needle piercing accidents after use.

In addition, with the relative rotation of the outer cylinder 4 with respect to the cover member 6, each of the spurs 613 of the cover member 6 is engaged with the long hole 44b from the groove 46b (initial state) of the outer cylinder 4, and the state of the device is less likely to return to its initial state compared to a straight advance type device through the function of the safety mechanism and the state before and after use can be easily recognized, and therefore, it is possible to prevent reuse of the device. Furthermore, it is possible to safely and reliably dispose of the used liquid administration device 10 without mistaking the used device for a liquid administration device 10 before use.

In addition, the spur 63 of the cover member 6 moves relative to the cover member 6 along the linear groove 423 in the distal direction, and when the cover member 6 is at the fifth position, the spur 63 of the cover member 6 is positioned at the position shown in FIG. 40 with respect to the outer cylinder 4.

As described above, according to the liquid administration device 10, it is possible to support the movement of the operation member 5 in the distal direction using the biasing force of the coil spring 9, that is, the auxiliary force thereof. Accordingly, for example, it is possible to easily and reliably administer a liquid even when using a relatively thin double ended needle 71 and administering a liquid with a relatively high viscosity. In addition, for example, it is possible to easily and reliably administer a liquid even for users who have difficulty in performing the pressing operation of the operation member 5, for example, an elderly person, a female, or the like with a weak amount of force, and a patient with rheumatism who has a pain or deformation in the fingers.

In addition, it is possible to administer a liquid at a user's pace since the biasing force of the coil spring 9 can be used as the auxiliary force of the pressing operation.

In addition, when the coil spring 9 is extended, it is possible to prevent or suppress the ring of the winding wire of the coil spring 9 from being deviated in a radial direction, and accordingly, it is possible to prevent the coil spring 9 from being brought into contact with the outer peripheral surface of the plunger 51 by defining the positions of the hooks 91 and 92 when seen from the axial direction of the coil spring 9. Accordingly, it is possible to smoothly and reliably administer a liquid.

In addition, the operation of puncturing a living body with the double ended needle 71, the rotational operation of the outer cylinder 4, and the pressing operation of the operation member 5 can be smoothly performed as a continuous operation.

In addition, when being set to the released state, the outer cylinder 4 obtains propulsive force in the rotational direction using the coil spring 9 and the slope 491a, and accordingly, it is possible to easily rotate the outer cylinder 4.

Note that, in the present invention, the cover member 6 or the coil spring 13 may be omitted.

When the coil spring 13 is omitted, F0 and F1 are preferably set so as to satisfy the following equation (2).

$$F1 \leq F0 \qquad (2)$$

Sixth Embodiment

Figure 43:
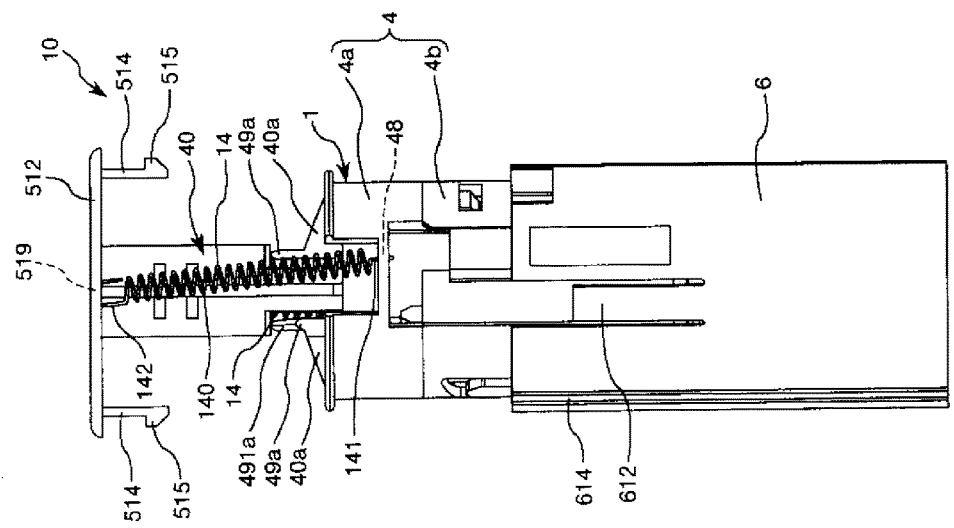
FIG. 43 is a side view showing a sixth embodiment of a liquid administration device of the present invention.
Figure 44:
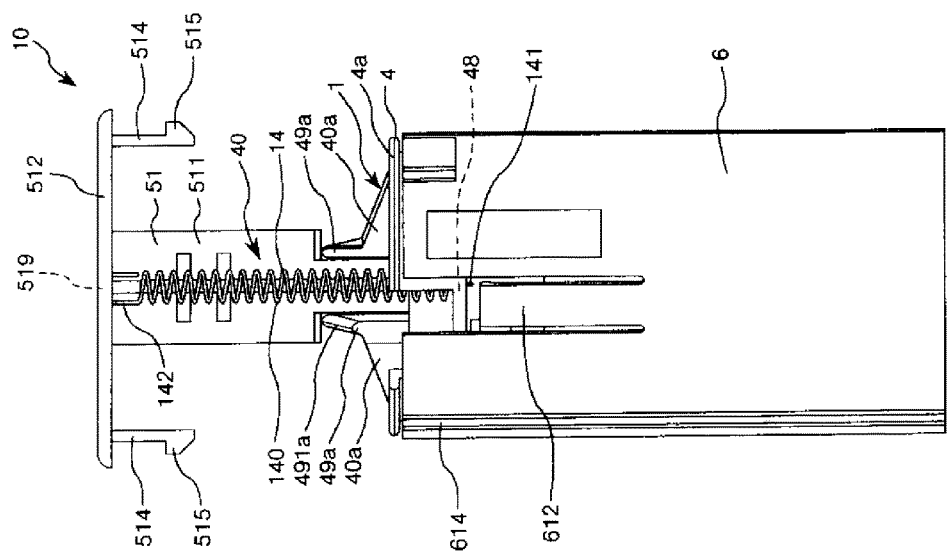
FIG. 44 is a second side view of the liquid administration device shown in FIG. 43.

FIGS. 43 and 44 are side views showing a sixth embodiment of a liquid administration device of the present invention. FIG. 43 is a view corresponding to FIGS. 24 and 25, and FIG. 44 is a view corresponding to FIGS. 36 and 37. Note that, hereinafter, the upper side is described as "proximal end (rear end)" or "upper (upward)", the lower side is described as "distal end" or "lower (downward), and the vertical direction is described as "axial direction" or "longitudinal direction" in FIGS. 43 and 44. In addition, some members are not shown in FIGS. 43 and 44 in order to show a structure of the inside of the liquid administration device.

Hereinafter, in regard to the sixth embodiment, the difference between the sixth embodiment and the aforementioned fifth embodiment will be mainly described, and the description of the same matter will not be repeated.

As shown in FIGS. 43 and 44, in the liquid administration device 10 of the sixth embodiment, an auxiliary mechanism 40 has a plurality of coil springs (two in the structure in the drawings) 14. In addition, each of the coil springs 14 is a tension spring used in a state of being extended. The coil springs 14 are arranged at equiangular intervals along the outer periphery of a plunger 51 so as to face each other when seen from the axial direction of the plunger 51. That is, the plunger 51 is disposed outside the coil springs 14 when seen from the axial direction of each of the coil springs 14. Note that the coil springs 14 are the same as each other, and therefore, one coil spring 14 will be representatively described below.

The coil spring 14 has a coil spring main body 140; a hook 141 as a first attachment portion which is provided in the distal portion of the coil spring main body 140 and attached to an inner structure 1; and a hook 142 as a second attachment portion which is provided in the proximal portion of the coil spring main body 140 and attached to an operation member 5.

In addition, an outer cylinder 4 of the inner structure 1 has a support portion 48 as a structure side attachment portion to which the hook 141 of the coil spring 14 is attached. In addition, the plunger 51 of the operation member 5 has a support portion 519 as an operation member side attachment portion to which the hook 142 of the coil spring 14 is attached, in a flange 512 of the plunger.

As shown in FIG. 43, the hook 141 is placed in the support portion 48 of the outer cylinder 4 and the hook 142 is placed in the support portion 519 of a rib 5130 of the plunger 51 (refer to FIG. 43) in a state where the coil spring 14 is extended and twisted around a central axis of the outer cylinder 4 in an unused state (initial state). In addition, when seen from the axial direction of the coil spring 14, the support portion 48 and the support portion 519 are deviated from each other in the initial state, that is, a state before the outer cylinder 4 is rotated. Accordingly, the coil spring 9 biases one of the outer cylinder 4 and the operation member 5 to the other in a rotational direction around the central axis of the cylindrical body 2.

As shown in FIG. 44, when seen from the axial direction of the coil spring 14, the support portion 48 and the support portion 519 are coincident with each other after the outer cylinder 4 is rotated. Accordingly, biasing force of the coil spring 14 in the rotational direction disappears, and therefore, it is possible to prevent the outer cylinder 4 from being rotated by the biasing force of the coil spring.

According to the liquid administration device 10, the same effect as that in the aforementioned fifth embodiment can be obtained.

Note that, in the present invention, the number of coil springs 14 is not limited to two, and examples thereof may include one or three or greater.

Seventh Embodiment

Figure 45:
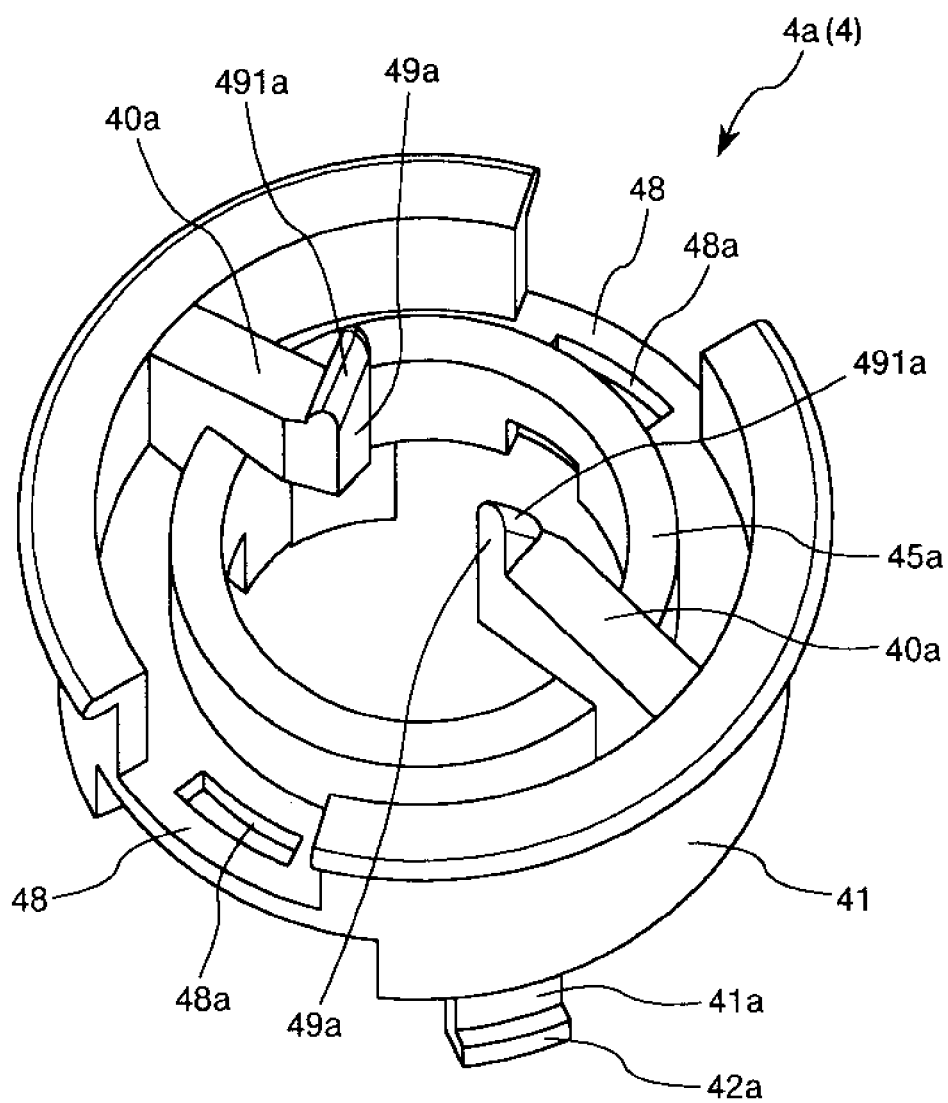
FIG. 45 is a perspective view of a proximal side member of an outer cylinder of a cylindrical body in a seventh embodiment of a liquid administration device of the present invention.

FIG. 45 is a perspective view of a proximal side member of an outer cylinder of a cylindrical body in a seventh embodiment of a liquid administration device of the present invention. Note that, hereinafter, the upper side is described as "proximal end (rear end)" or "upper (upward)", the lower side is described as "distal end" or "lower (downward), and the vertical direction is described as "axial direction" or "longitudinal direction" in FIG. 45.

Hereinafter, in regard to the seventh embodiment, the difference between the seventh embodiment and the aforementioned sixth embodiment will be mainly described, and the description of the same matter will not be repeated.

In the liquid administration device 10 of the seventh embodiment, each of a coil springs 14 is not twisted in a circumferential direction in an unused state (initial state).

In addition, as shown in FIG. 45, two grooves 48a extending in a circumferential direction of a proximal side member 4a are formed in the proximal side member 4a of the outer cylinder 4, and two support portions 48 are formed on an outer peripheral side of each of the grooves 48a. The support portions 48 are arranged at equiangular intervals so as to face each other, that is, along the circumferential direction of the proximal side member 4a, and the grooves 48a are arranged at equiangular intervals so as to face each other, that is, along the circumferential direction of the proximal side member 4a. Note that each of the support portions 48 and each of the grooves 48a are the same as each other, and therefore, one of the support portions 48 and one of the grooves 48a will be representatively described below.

First, the length of the groove 48a is set to a length corresponding to the amount of rotation of the outer cylinder 4. Note that, needless to say, the length of the groove 48a may be set to be longer than the length described above.

In the coil spring 14, the hook 141 is placed in the support portion 48 by being inserted into the groove 48a of the outer cylinder 4, and the hook 142 is placed in the support portion 519 of a rib 5130 of the plunger 51. Accordingly, the hook 141 can move to the outer cylinder 4 along the groove 48a. Accordingly, it is possible to prevent the coil spring 14 from being twisted when the outer cylinder 4 is rotated.

According to the liquid administration device 10, the same effect as that in the aforementioned sixth embodiment can be obtained.

Note that the seventh embodiment can also be applied to the fifth electrode.

Hereinbefore, although the liquid administration device of the present invention has been described based on the embodiments shown in the drawings, the present invention is not limited thereto, and the configuration of each portion can be replaced with an arbitrary configuration which has an identical function. In addition, other arbitrary component may be added to the present invention.

In addition, the present invention may be obtained by combining two or more arbitrary configurations (characteristics) of each of the embodiments.

In addition, in the embodiments, the cylindrical body is filled with a liquid in advance, but the present invention is not limited thereto, and for example, the cylindrical body may not be initially filled with a liquid and used by filling with a liquid later.

In addition, in the embodiments, the first biasing member is a compression spring, but the present invention is not limited thereto. For example, the first biasing member may be a tension spring and anything other than the spring.

In addition, in the embodiments, the second biasing member is a tension spring, but the present invention is not limited thereto. For example, the second biasing member may be a compression spring and anything other than the spring.

In addition, in the embodiments, the second biasing member also serves as the third biasing member, but the present invention is not limited thereto. For example, an exclusive third biasing member may be provided without sharing the second biasing member or the like. Note that, examples of the third biasing member include a tension spring and a compression spring, anything other than the spring may be employed.

In addition, in the embodiments, the cylindrical body in which a gasket slides therein is constituted by two members including an inner cylinder and an outer cylinder, but the present invention is not limited thereto, and may be constituted by one member.

In addition, in the embodiments, the first engagement portion of the engagement mechanism (engagement portion) is provided in the operation member and the second engagement portion is provided in the inner structure. However, the present invention is not limited thereto, and for example, the first engagement portion may be provided in the inner structure and the second engagement portion may be provided in the operation member.

A liquid administration device of the present invention includes: an inner structure that includes a cylindrical body which has a bottom part in a distal portion and an opening portion in a proximal portion and can be filled with a liquid therein, a needle tube which is mounted in the distal portion of the cylindrical body and has a sharp needle tip at a distal end, and a proximal end of which is communicatable with the inside of the cylindrical body, and a gasket which is installed in the cylindrical body and is slidable along an axial direction of the cylindrical body; an operation member which has a plunger pressing the gasket and performs a pressing operation in which the plunger is moved to the cylindrical body toward a distal direction while being pressed; an engagement mechanism (engagement portion) that includes a first engagement portion which is provided in one of the inner structure and the operation member and a second engagement portion which is provided in the other one of the inner structure and the operation member, in which the engagement mechanism enters an engagement state where the pressing operation is inhibited when the first engagement portion and the second engagement portion are engaged with each other, and enters a released state where the pressing operation can be performed when the engagement state is released; and a rotary mechanism (rotary portion) which makes the first engagement portion and the second engagement portion, being in the engagement state, relatively rotate around a central axis of the inner structure and enter the released state.

According to certain embodiments of the present invention, the first engagement portion and the second engagement portion which are in the engagement state are made to relatively rotate around the central axis of the inner structure to be set to the released state. Therefore, the direction of relative displacement of the first engagement portion and the second engagement portion, when making them enter the released state, is different from the direction of the pressing operation of the operation member. Accordingly, it is possible to prevent the first engagement portion and the second engagement portion from unintentionally entering the released state and to prevent a liquid from unintentionally leaking from the needle tube before or in the middle of puncturing of the skin with the needle tube.

What is claimed is:

1. A liquid administration device comprising:
    an inner structure that includes:
        a cylindrical body comprising:
            an inner cylinder that has a bottom part in a distal portion thereof and an opening portion in a proximal portion thereof, the inner cylinder being fillable with a liquid,
            an outer cylinder that is concentric with the inner cylinder and extends around an outer periphery of the inner cylinder, the outer cylinder being rotatable relative to the inner cylinder around a central axis of the inner structure,
        a needle tube that is mounted in the distal portion of the cylindrical body and has a sharp needle tip at a distal end and a proximal end of which is communicatable with an inside of the cylindrical body, and
        a gasket that is located in the cylindrical body and is slidable in an axial direction of the cylindrical body;
    an operation member that includes a plunger configured to press the gasket, the operation member being configured to perform a pressing operation in which the plunger is moved relative to the cylindrical body in a distal direction while being pressed;
    wherein the plunger comprises:
        an elongated plate-shaped part, and
        a first engagement portion that comprises at least one stepped portion in which a width of the elongated plate-shaped part changes;
    wherein the outer cylinder comprises a second engagement portion;
    wherein the first and second engagement portions are configured to enter an engaged state in which the first engagement portion and the second engagement portion are engaged with each other, and the pressing operation is inhibited, and
    wherein the first and second engagement portions are configured to enter a released state in which the first engagement portion and the second engagement portion are disengaged, and the pressing operation is performable; and
    a rotary portion configured to cause the first engagement portion and the second engagement portion to relatively rotate around a central axis of the of the inner structure and thereby move from the engagement state to the released state.

2. The liquid administration device according to claim 1, further comprising a rotation inhibiting portion configured to selectively inhibit the relative rotation of the first engagement portion and the second engagement portion around the central axis of the inner structure in the engaged state.

3. The liquid administration device according to claim 1, wherein the second engagement portion includes at least one protruding portion that protrudes toward the inside of the cylindrical body.

4. The liquid administration device according to claim 3, wherein the second engagement portion includes a slope located at an end portion of the protruding portion and on which the first engagement portion abuts.

5. The liquid administration device according to claim 4, wherein the outer cylinder is rotatable relative to the operation member around the central axis of the outer cylinder due to the first engagement portion moving relative to the second engagement portion along the slope.

6. The liquid administration device according to claim 1, further comprising a cover member that is movable between a position (A) at which at least the needle tip of the needle tube is covered and a position (B) at which the needle tip is exposed from the cover member and a liquid is dischargeable through the needle tube due to the cover member being retreated in a proximal direction from the position (A).

7. The liquid administration device according to claim 5, further comprising a cover member that is movable between a position (A) at which at least the needle tip of the needle tube is covered and a position (B) at which the needle tip is exposed from the cover member and a liquid is dischargeable through the needle tube due to the cover member being retreated in a proximal direction from the position (A).

8. The liquid administration device according to claim 6, wherein the first and second engagement portions are configured such that the first and second engagement portions enter the engaged state when the cover member is positioned at the position (A) and enter the released state when the engaged state is released by the cover member moving to the position (B).

9. The liquid administration device according to claim 7, wherein the first and second engagement portions are configured such that the first and second engagement portions enter the engaged state when the cover member is positioned at the position (A) and enter the released state when the engaged state is released by the cover member moving to the position (B).

10. The liquid administration device according to claim 6, wherein the rotary portion includes:
   a spur that is provided in one of the cover member and the outer cylinder, and
   an inclined first groove that is provided in the other of the cover member and the outer cylinder and into which the spur is insertable, and
wherein the outer cylinder is configured such that the outer cylinder is rotatable relative to the cover member around the central axis by the spur moving relative to the cover member along the first groove such that the outer cylinder is rotated relative to the operation member around the central axis of the outer cylinder.

11. The liquid administration device according to claim 8, wherein the rotary portion includes:
   a spur that is provided in one of the cover member and the outer cylinder, and
   an inclined first groove that is provided in the other of the cover member and the outer cylinder and into which the spur is inserted, and
wherein the outer cylinder is configured such that the outer cylinder is rotatable relative to the cover member around the central axis by the spur moving relative to the cover member along the first groove such that the outer cylinder is rotated relative to the operation member around the central axis of the outer cylinder.

12. The liquid administration device according to claim 9, wherein the rotary portion includes:
   a spur that is provided in one of the cover member and the outer cylinder, and
   an inclined first groove that is provided in the other of the cover member and the outer cylinder and into which the spur is inserted, and
wherein the outer cylinder is configured such that the outer cylinder is rotatable relative to the cover member around the central axis by the spur moving relative to the cover member along the first groove such that the outer cylinder is rotated relative to the operation member around the central axis of the outer cylinder.

13. The liquid administration device according to claim 12, wherein the rotary portion includes a biasing member configured to bias one of the first engagement portion and the second engagement portion to the other of the first engagement portion and the second engagement portion in a rotational direction of the inner structure around the central axis.

14. The liquid administration device according to claim 13, wherein the biasing member is twisted in an initial state.

15. The liquid administration device according to claim 1,
   wherein the rotary portion includes a biasing member configured to bias one of the first engagement portion and the second engagement portion to the other of the first engagement portion and the second engagement portion in a rotational direction of the inner structure around the central axis,
wherein the biasing member is twisted in an initial state.

16. The liquid administration device according to claim 6,
   wherein the rotary portion includes a biasing member configured to bias one of the first engagement portion and the second engagement portion to the other of the first engagement portion and the second engagement portion in a rotational direction of the inner structure around the central axis,
wherein the biasing member is twisted in an initial state.

17. The liquid administration device according to claim 1,
   wherein the second engagement portion includes a slope on which the first engagement portion abuts, and
wherein the outer cylinder is rotatable relative to the operation member around the central axis of the outer cylinder due to the first engagement portion moving relative to the second engagement portion along the slope.

* * * * *